United States Patent [19]

Ziegler

[11] Patent Number: 5,447,860
[45] Date of Patent: Sep. 5, 1995

[54] TYROSINE KINASE

[75] Inventor: Steven F. Ziegler, Seattle, Wash.

[73] Assignee: Immunex Corporation, Seattle, Wash.

[21] Appl. No.: 323,474

[22] Filed: Oct. 14, 1994

Related U.S. Application Data

[63] Continuation of Ser. No. 905,600, Jun. 26, 1992, abandoned.

[51] Int. Cl.$^6$ .............. C12N 5/10; C12N 15/54; C12N 1/15; C12N 1/21; C12N 15/63
[52] U.S. Cl. .............. 435/240.1; 435/252.3; 435/254.11; 435/320.1; 435/194; 536/23.2; 536/23.5
[58] Field of Search .......... 435/69.1, 69.2, 320.1, 435/240.1, 252.3, 254.11, 194; 536/23.2, 23.5

[56] References Cited

PUBLICATIONS

Ziegler et al (1993) Oncogene 8:663–670.
Flanagan et al. (1990) Cell 63 185–194.
Partanen et al., "Putative tyrosine kinases expressed in K-562 human leukemia cells" *Proc. Natl. Acad. Sci. USA* 87:8913–8917, 1990.
Partanen et al., "A Novel Endothelial Cell Surface Receptor Tyrosine Kinase with Extracellular Epidermal Growth Factor Homology Domians" *Mol. Cell. Biol.* 12:1698–1707, 1992.
Wilks, "Tow putative protein-tyrosine kinases identified by application of the polymerase chain reaction" *Proc. Natl. Acad. Sci. USA* 86:1603–1607, 1989.
Yarden and Ullrich, "Growth Factor Receptor Tyrosine Kinases" *Ann. Rev. Biochem.* 57:443–78, 1988.
Hirai et al., "A Novel Putative Tyrosine Kinase Receptor Encoded by the eph Gene" *Science* 238:1717–1720, 1987.
Lindberg and Hunter, "cDNA Cloning and Characterization of eck, and Epithelial Cell Receptor Protein-Tyrosine Kinase in the *eph/elk* Family of Protein Kinases" *Mol. Cell. Biol.* 10:6316–6324, 1990.
Hanks et al., "The Protein Kinase Family: Conserved Features and Deduced Phylogeny of the Catalytic Domains" *Science* 241:42–52, 1988.
Ullrich and Schlessinger, "Signal Transduction by Receptors with Tyrosine Kinase Activity" *Cell* 61:203–212, 1990.
O'Bryan et al., "axl, a Transforming Gene Isolated from Primary Human Myeloid Leukemia Cells, Encodes a Novel Receptor Tyrosine Kinase" *Mol. Cell. Biol.* 11:5016–5031, 1991.
Rescigno et al., "A putative receptor tyrosine kinase with unique structural topology" *Oncogene* 6:1909–1913, 1991.
Lhotak et al., "Characterization of Elk, a Brain-Specific Receptor Tyrosine Kinase" *Mol. Cell. Biol.* 11:2496–2502, 1991.
Chan and Watt, "*eek* and *erk*, new members of the *eph* subclass of receptor protein-tyrosine kinases" *Oncogene* 6:1057–1061, 1991.
Sasaki et al., "Laminin, a Multidomain Protein" *J. Biol. Chem.* 263:16536–16544, 1988.
Ellisen et al., "TAN-1, the Human Homolog of the Drosophila Notch Gene, Is Broken by Chromosomal Translocations in T Lymphoblastic Neoplasms" *Cell* 66:649–661, 1991.

(List continued on next page.)

Primary Examiner—Charles L. Patterson, Jr.
Assistant Examiner—G. E. Bugaisky
Attorney, Agent, or Firm—Kathryn A. Anderson

[57] ABSTRACT

A novel receptor protein tyrosine kinase named ork (orphan receptor tyrosine kinase) is identified and characterized. cDNA encoding the ork protein is inserted into an expression vector for production of the protein via recombinant DNA technology. The ork cDNA, when transfected into Cos-7 cells, encodes a 140 Kd protein with in vitro kinase activity. The ork gene is expressed predominantly in placenta and lung, with lower levels in umbilical vein endothelial cells, brain and kidney.

10 Claims, 18 Drawing Sheets

PUBLICATIONS

Williams and Barclay, "The Immunoglobulin Superfamily-Domains for Cell Surface Recognition" *Ann. Rev. Innumol.* 6:381–405, 1988.

Takahashi and Cooper, "ret Transforming Gene Encodes a Fusion Protein Homologous to Tyrosine Kinases" *Mol. Cell. Biol.* 7:1378–1385, 1987.

Margolis et al., "EGF Induces Tyrosine Phosphorylation of Phospholipase C-II: A Potential Mechanism for EGF Receptor Signaling" *Cell* 57:1101–1107, 1989.

Terman et al., "Identification of a new endothelial cell growth factor receptor tyrosine kinase" *Oncogene* 6:1677–1683, 1991.

Aprelikova et al., "FLT4, a Novel Class III Receptor Tyrosine Kinase in Chromosome 5q33-qter" *Cancer Research* 52:746–748, 1992.

Matthews et al., "A Receptor Tyrosine Kinase Specific to Hematopoietic Stem and Progenitor Cell-Enriched Populations" *Cell* 65:1143–1152, 1991.

Reid et al., "Two forms of the basic fibroblast growth factor receptor-like mRNA are expressed in the developing mouse brain" *Proc. Natl. Acad. Sci. USA* 87:1596–1600, 1990.

Raz et al., "PCR-based identification of new receptors: molecular cloning of a receptor for fibroblast growth factors" *Oncogene* 753–760, 1991.

Lai and Lemke, "An Extended Family of Protein-Tyrosine Kinase Genes differentially Expressed in the Vertebrate Nervous System" *Neuron* 6:691–704, 1991.

FIGURE 1a

```
                    CTTCTGTGCTGTTCCTTCTTGCCTCTAA           28
CTTGTAAACAAGACGTACTAGGACGATGCTAAATGGAAAGTCACAAACC          76
GCTGGGTTTTGAAAGGATCCCTGGGACCTCATGCACACATTGTGGAAA          124
CTGGATGGAGAGATTTGGGGAAGCCATGGACTCTTTAGCCAGCTTAGTT         172
                     M  D  S  L  A  S  L  V
CTCTGTGGAGTCAGCTTGCTCCTTTCTGGAACTGTGGAAGGTGCCATG          220
 L  C  G  V  S  L  L  L  S  G  T  V  E  G  A  M
GACTTGATCTTGATCAATTCCCTACCCTCTTGTATCTGATGCTGAAACA         268
 D  L  I  L  I  N  S  L  P  L  V  S  D  A  E  T
TCTCTCACCTGCATTGCCCTCTGGGGCGCCCCATGAGCCCATCACC            316
 S  L  T  C  I  A  S  G  W  R  P  H  E  P  I  T
ATAGGAAGGGACTTTGAAGCCCTTAATGAACCAGGACCACCAGGATCCGCTG      364
 I  G  R  D  F  E  A  L  M  N  Q  H  Q  D  P  L
GAAGTTACTCAAGATGTGACCAGAGAATGGGCTAAAAAGTTGTTTGG           412
 E  V  T  Q  D  V  T  R  E  W  A  K  K  V  V  W
AAGAGAGAAAAGGCTAGTAAGATCAATGGTGCTTATTCTGTGAAGGG           460
 K  R  E  K  A  S  K  I  N  G  A  Y  F  E  G
```

```
     CGAGTTCGAGGAGAGGCAATCAGGATACGAACCATGAAGATGCGTCAA    508
105   R  V  R  G  E  A  I  R  I  R  T  M  K  M  R  Q

CAAGCTTCCTTCCTACCAGCTACTTTAACTATGACTTGATGACTGTGGACAAGGA    556
121   Q  A  S  F  L  P  A  T  L  T  M  T  V  D  K  G

GATAACGTGAACATATCTTTCAAAAAGGTATTGATTAAAGAAGAAGAT    604
137   D  N  V  N  I  S  F  K  K  V  L  I  K  E  E  D

GCAGTGATTTACAAAAATGGTTCCTTCATTCATCCAGTGCCCCGGCAT    652
153   A  V  I  Y  K  N  G  S  F  I  H  S  V  P  R  H

GAAGTACCTGATATTCTAGAAGTACACCTGCCTCATGCTCAGCCCCAG    700
169   E  V  P  D  I  L  E  V  H  L  P  H  A  Q  P  Q

GATGCTGGAGTGTACTCGGCCAGGTATATAGGAGAAACCTTCTTCACC    748
185   D  A  G  V  Y  S  A  R  Y  I  G  G  N  L  F  T

TCGGCCTTCACCAGGCTGATAGTCCGGAGATGTGAAGCCCAGAAGTGG    796
201   S  A  F  T  R  L  I  V  R  R  C  E  A  Q  K  W

GGACCTGAATGCAACCATCTCTGTACTGTTGTATGAACAATGGTGTC    844
217   G  P  E  C  N  H  L  C  T  A  C  M  N  N  G  V

TGCCATGAAGATACTGGAGAATGCATTTGCCCTCCTGGGTTTATGGGA    892
233   C  H  E  D  T  G  E  C  I  C  P  P  G  F  M  G

AGGACGTGTGAGAAGGCTTGTGAACTGCACACGTTTGGCAGAACTTGT    940
249   R  T  C  E  K  A  C  E  L  H  T  F  G  R  T  C
```

FIGURE 1c

```
265  AAAGAAAGGTGCAGTGGACAAGAGGGATGCAAGTCTTATGTGTTCTGT      988
      K  E  R  C  S  G  Q  E  G  C  K  S  Y  V  F  C
281  CTCCCTGACCCCTATGGGTGTTCCTGTGCCACAGGCTGGAAGGGTCTG     1036
      L  P  D  P  Y  G  C  S  C  A  T  G  W  K  G  L
297  CAGTGCAATGAAGCATGCCACCCTGGTTTTTACGGGCCAGATTGTAAG     1084
      Q  C  N  E  A  C  H  P  G  F  Y  G  P  D  C  K
313  CTTAGGTGCAGCTGCAACAATGGGGAGATGTGTGATCGCTTCCAAGGA     1132
      L  R  C  S  C  N  N  G  E  M  C  D  R  F  Q  G
329  TGTCTCTGCTCTCCAGGATGGCAGGGCTCCAGTGTGAGAGAGAAGGC     1180
      C  L  C  S  P  G  W  Q  G  L  Q  C  E  R  E  G
345  ATACCGAGGATGACCCCAAAGATAGTGGATTTGCCAGATCATATAGAA     1228
      I  P  R  M  T  P  K  I  V  D  L  P  D  H  I  E
361  GTAAACAGTGGTAAATTTAATCCCATTTGCAAAGCTTCTGGCTGGCCG     1276
      V  N  S  G  K  F  N  P  I  C  K  A  S  G  W  P
377  CTACCTACTAATGAAGAAATGACCCTGGTTAAGCCGGATGGGACAGTG     1324
      L  P  T  N  E  E  M  T  L  V  K  P  D  G  T  V
393  CTCCATCCAAAAGACTTTAACCATGACCATTTCTCAGTAGCCATA      1372
      L  H  P  K  D  F  N  H  D  H  F  S  V  A  I
409  TTCACCATCCACCGGATCCTCCCCCCTGACTCAGGAGTTTGGGTCTGC     1420
      F  T  I  H  R  I  L  P  P  D  S  G  V  W  V  C
```

FIGURE 1d

```
425  AGTGTGAACACAGTGGCTGGGATGGTGGAAAAGCCCTTCAACATTCT   1468
     S  V  N  T  V  A  G  M  V  E  K  P  F  N  I  S
441  GTTAAAGTTCTTCCAAAGCCCCTGAATGCCCCAAACGTGATTGACACT   1516
     V  K  V  L  P  K  P  L  N  A  P  N  V  I  D  T
457  GGACATAACTTTGCTGTCATCAACATCAGCTCTGAGCCTTACTTTGGG   1564
     G  H  N  F  A  V  I  N  I  S  S  E  P  Y  F  G
473  GATGGACCAATCAAATCCAAGAAGCTTCTATACAAACCCGTTAATCAC   1612
     D  G  P  I  K  S  K  K  L  L  Y  K  P  V  N  H
489  TATGAGGCTTGGCAACATATTCAAGTGACAAATGAACTCTGTGCAACTGGTC   1660
     Y  E  A  W  Q  H  I  Q  V  T  N  E  I  V  T  L
505  AACTATTTGGAACCTCGGACAGAATATGAACTCTGTGTGCAACTGGTC   1708
     N  Y  L  E  P  R  T  E  Y  E  L  C  V  Q  L  V
521  CGTCGTGGAGAGGGTGGGGAAGGGCATCCTGGACCTGTGAGACGCTTC   1756
     R  R  G  E  G  G  E  G  H  P  G  P  V  R  R  F
537  ACAACAGCTTCTATCGGACTCCCTCCTCCCAAGAGTCTAAATCTCCTG   1804
     T  T  A  S  I  G  L  P  P  P  R  G  L  N  L  L
553  CCTAAAAGTCAGACCACTCTAAATTTGACCTGGCAACCAATATTTCCA   1852
     P  K  S  Q  T  T  L  N  L  T  W  Q  P  I  F  P
569  AGCTCGGAAGATGACTTTTATGTTGAAGTGGAGAGAAGGTCTGTGCAA   1900
     S  S  E  D  D  F  Y  V  E  V  E  R  R  S  V  Q
```

FIGURE 1e

| | | |
|---|---|---|
| 585 | AAAAGTGATCAGCAGAATATTAAAGTTCCAGGGCAACTTGACTTCGGTG<br>K  S  D  Q  Q  N  I  K  V  P  G  N  L  T  S  V | 1948 |
| 601 | CTACTTAACAACTTACATCCCAGGGAGCAGTACGTGGTCCGAGCTAGA<br>L  L  N  N  L  H  P  R  E  Q  Y  V  V  R  A  R | 1996 |
| 617 | GTCAACACCAAGGCCCAGGGGGAATGGAGTGAAGATCTCACTGCTTGG<br>V  N  T  K  A  Q  G  E  W  S  E  D  L  T  A  W | 2044 |
| 633 | ACCCTTAGTGACATTCTTCCTCCTCAACCAGAAAACATCAAGATTTCC<br>T  L  S  D  I  L  P  P  Q  P  E  N  I  K  I  S | 2092 |
| 649 | AACATTACACACTCCCTCGGCTGTGATTTCTTGGACAATATTGGATGGC<br>N  I  T  H  S  S  A  V  I  S  W  T  I  L  D  G | 2140 |
| 665 | TATTCTATTTCTTCTATTACTATCCGTTACAAGGTTCAAGGCAAGAAT<br>Y  S  I  S  S  I  T  I  R  Y  K  V  Q  G  K  N | 2188 |
| 681 | GAAGACCAGCACGTTGATGTGAAAGATAAAGAATGCCACCATCATTCAG<br>E  D  Q  H  V  D  V  K  I  K  N  A  T  I  I  Q | 2236 |
| 697 | TATCAGCTCAAGGCCTAGAGCCTGAAACATAGGCATACCAGGTGGACATT<br>Y  Q  L  K  G  L  E  P  E  T  A  Y  Q  V  D  I | 2284 |
| 713 | TTTGCAGAGAACAACATAGGGTCAAGCAACCCAGCCTTTCTCATGAA<br>F  A  E  N  N  I  G  S  S  N  P  A  F  S  H  E | 2332 |
| 729 | CTGGTGACCCTCCCAGAATCTCAAGCACCCAGCGGACCTCGGAGGGGG<br>L  V  T  L  P  E  S  Q  A  P  A  D  L  G  G  G | 2380 |

FIGURE 1f

```
745  AAGATGCTGCTTATAGCCATCCTTGGCTCTGCTGGAATGACCTGCCTG          2428
      K  M  L  L  I  A  I  L  G  S  A  G  M  T  C  L
761  ACTGTGCTGTTGGCCTTTCTGATCATATTGCAATTGAAGAGGGCAAAT          2476
      T  V  L  L  A  F  L  I  I  L  Q  L  K  R  A  N
777  GTGCAAAGGAGAATGGCCCAAGCCTTCCAAAACGTGAGGGAAGAACCA          2524
      V  Q  R  R  M  A  Q  A  F  Q  N  V  R  E  E  P
793  GCTGTGCAGTTCAACTCAGGGACTCTGGCCCTAAAACAGGAAGGTCAAA         2572
      A  V  Q  F  N  S  G  T  L  A  L  N  R  K  V  K
809  AACAACCCAGATCCTACAATTTATCCAGTGCTTGACTGGAATGACATC          2620
      N  N  P  D  P  T  I  Y  P  V  L  D  W  N  D  I
825  AAATTTCAAGATGTGATTGGGGAGGGCAATTTTGGCCAAGTTCTTAAG          2668
      K  F  Q  D  V  I  G  E  G  N  F  G  Q  V  L  K
841  GCGGCCATCAAGAAGGATGGGTTACGGATGGATGCTGCCATCAAAAGA          2716
      A  A  I  K  K  D  G  L  R  M  D  A  A  I  K  R
857  ATGAAAGAATATGCCTCCAAAGATGATCACAGGGACTTTGCAGGAGAA         2764
      M  K  E  Y  A  S  K  D  D  H  R  D  F  A  G  E
873  CTGGAAGTTCTTTGTAAACTTGGACACCATCCAAACATCAATCTC            2812
      L  E  V  L  C  K  L  G  H  H  P  N  I  I  N  L
889  TTAGGAGCATGTGAACATGAGGCTACTTGTACCTGGCCATTGAGTAC          2860
      L  G  A  C  E  H  R  G  Y  L  Y  L  A  I  E  Y
```

FIGURE 1g

```
905  GCGCCCCATGGAAACCTTCTGGACTTCCTTCGCAAGAGCCGTGTGCTG  2908
      A  P  H  G  N  L  L  D  F  L  R  K  S  R  V  L
921  GAGACGGACCCCAGCATTTGCCATTGCCAATAGCACCGCGTCCACACTG  2956
      E  T  D  P  A  F  A  I  A  N  S  T  A  S  T  L
937  TCCTCCCAGCAGCTCCTTCACTTCGCTGCCGACGTGGCCCGGGGCATG  3004
      S  S  Q  Q  L  H  F  A  A  D  V  A  R  G  M
953  GACTACTTGAGCCAAAAACAGTTTATCCACAGGGATCTGGCTGCCAGA  3052
      D  Y  L  S  Q  K  Q  F  I  H  R  D  L  A  A  R
969  AACATTTTAGTTGGTGAAAACTATGTGGCAAAAATAGCAGATTTTGGA  3100
      N  I  L  V  G  E  N  Y  V  A  K  I  A  D  F  G
985  TTGTCCCGAGGTCAAGAGGTGTACGTGAAAAAGACAATGGGAAGGCTC  3148
      L  S  R  G  Q  E  V  Y  V  K  K  T  M  G  R  L
1001 CCAGTGCGCTGGATGGCCATCGAGTCACTGAATTACAGTGTGTACACA  3196
      P  V  R  W  M  A  I  E  S  L  N  Y  S  V  Y  T
1017 ACCAACAGTGATGTATGGTCCTATGGTGTGTTACTATGGGAGATTGTT  3244
      T  N  S  D  V  W  S  Y  G  V  L  L  W  E  I  V
1033 AGCTTAGGAGGCACACCCTACTGCGGGATGACTTGTGCAGAACTCTAC  3292
      S  L  G  G  T  P  Y  C  G  M  T  C  A  E  L  Y
1049 GAGAAGCTGCCCCAGGGCTACAGACTGGAGAAGCCCCTGAACTGTGAT  3340
      E  K  L  P  Q  G  Y  R  L  E  K  P  L  N  C  D
```

FIGURE 1h

```
1065  GATGAGGTGTATGATCTAATGAGACAATGCTGGGGGGAGAAGCCTTAT  3388
      D   E   V   Y   D   L   M   R   Q   C   W   R   E   K   P   Y
      GAGAGGCCATCATTGCCCAGATATTGGTGTCCTTAAACAGAATGTTA  3436
1081  E   R   P   S   F   A   Q   I   L   V   S   L   N   R   M   L
      GAGGAGCGAAAGACCTACGTGAATACCACGCTTTATGAGAAGTTTACT  3484
1097  E   E   R   K   T   Y   V   N   T   T   L   Y   E   K   F   T
      TATGCAGGAATTGACTGTTCTGCTGAAGAGCGGCCTAGGACAGAACA  3532
1113  Y   A   G   I   D   C   S   A   E   E   A   A   *

TCTGTATACCCTCTGTTTCCCTTTCACTGGCATGGGAGACCCTTGACA  3580
      ACTGCTGAGAAACATGCCTCTGCCAAAGGATGTGATATATAAGTGTA  3628
      CATATGTGCTGGAATTCTAACAAGTCATAGGTTAATATTTAAGACACT  3676
      GAAAAATCTAAGTGATATAAATCAGATTCTCTCTCATTTTATCCC    3724
      TCACCTGTAGCATGCCAGTCCCCGTTTCATTTAGTCATGTGACCACTCT  3772
      GTCTTGTGTTCCACAGCCTGCAAGTTCAGTCCAGGATGCTAACATCT  3820
      AAAAATAGACTTAAATCTCATTGCTTACAAGCCTAAGAATCTTTAGAG  3868
      AAGTATACATAAGTTTAGGATAAAAATAATGGGATTTTCTTTTCTTTC  3916
      TCTGGTAATATTGACTTGTATATTTAAGAAATAACAGAAAGCCTGGG  3964
      TGACATTTGGGAGACATGTGACATTTATATATTGAATTAATATCCCTA  4012
```

FIGURE 1i

```
CATGTATTGCACATTGTAAAAAGTTTAGTTTTTGATGAGTTGTGAGTT    4060
TACCTTGTATACTGTAGGCACACTTTGCACTGATATATCATGAGTGAA    4108
TAAATGTCTTGCCTACTCAAAAAAAAAAAA                     4138
```

Figure 2

ORK-1  CEAQKWGPEC NHLCTA....CMNNGV.....CHEDT...GECIC PPGFMGRTC
ORK-2  CELHTFGRTC KERCSGQEGCCKS.YV....FCLPDPY.G.CSCATGWKGLQC
ORK-3  CHPGFYGPDC KLRCS....CNN.GE....MCDRFQ...G.CLCSPGWQGLQC

Figure 3B mock | ork
---|---
PI  C | PI  C

Kd
—200
←P140$^{ork}$
—97
—69 mock  *ork*
C  PI  C  PI

```
  1 .MDSLASLVLCGVSLLLSGTVEGAMDLILINSLPLVSDAETSLTCI....  45 ork
    :  .::..::|  . |:|.: |::|:||.|:...|.|....   |||:
  1 MVWRVPPFLL..PILFLASHVGAAVDLTLLANLRLTDPQRFFLTCVSGEA  48 tie 46 ASGWRPHE...PITIGRDFEALMNQHQDPLEVTQDVTREWAKKVVWKREK  92
    :.|:  ...   |: :::|   :......|| :...:..::    .::  .|
 49 GAGRGSDAWGPPLLLEKDDRIVRTPPGPPLRLARNGSHQ...VTLRGFSK  95

93 ASKINGAYFCEGRVRGEAIRIRTMKMRQQASFLPATLTMTVDKGDNVNIS 142
    :|.: |.: | | . : .|: :. ...| :||...:| ||:|||.. :|
 96 PSDLVGVFSCVGGAGARRTRVIYVHNSPGAHLLPDKVTHTVNKGDTAVLS 145

143 FKKVLIKEEDAVIYKNGSFIHSVPRHEVPD.ILEVHLPHAQPQDAGVYSA 191
    :   |:.|.:  .|||::...:.:||..|  :`::||:.||...|:||| 
146 ARVHKEKQTDVIWKSNGSYFYTLDWHEAQDGRFLLQLPNVQPPSSGIYSA 195

192 RYIGGNLFTSAFTRLIVRRCEAQKWGPECNHLCTACMNNGVCHEDTGECI 241
    |::::. :.||| |||||  |:|.:|||:|.. |.:|::.|||||:..|||:
196 TYLEASPLGSAFFRLIVRGCGAGRWGPGCTKECPGCLHGGVCHDHDGECV 245

242 CPPGFMGRTCEKACELHTFGRTCKERCSGQEGCKSYVFCLPDPYGCSCAT 291
    |||||  |  ||.||  ||..|.|.|.| .||::...|||||||||||:.
246 CPPGFTGTRCEQACREGRFGQSCQEQCPGISGCRGLTFCLPDPYGCSCGS 295

292 GWKGLQCNEACHPGFYGPDCKLRCSCNNGEMCDRFQGCLCSPGWQGLQCE 341
    ||:| ||.|||  || :|||:|.| |.||: |||| ||:|..||:|::||
296 GWRGSQCQEACAPGHFGADCRLQCQCQNGGTCDRFSGCVCPSGWHGVHCE 345

342 REGIPRMTPKIVDLPDHIEVNSGKFNPI.CKASGWPLPTNEEMTLVKPDG 390
    :.:  ..|.|::::...|.| :.: .| | |.| |:|...:.:.| ||||
346 KSD...RIPQILNMASELEFNLETMPRINCAAAGNPFPVRGSIELRKPDG 392

391 TVLHPKDFNHTDHFSVAIFTIHRILPPDSGVWVCSVNTVAGMVEKPFNIS 440
    |||  ...    ... ..| |.:.|:: :|||.| |.|.| :|    .:|.:-
393 TVLLSTKAIVEPEKTTAEFEVPRLVLADSGFWECRVSTSGGQDSRRFKVN 442

441 VKVLPKPLNAPNVIDTGHNFAVINISSEPYFGDPIKSKKLLYKPVNHYE 490
    ||| | ||.||.::  |  :. .:: . .: |||||.. :| |:|  :
443 VKVPPVPLAAPRLL.TKQSRQLVVSPLVSFSGDGPISTVRLHYRPQDSTM 491
```

Figure 5b

```
 491 AWQEIQV.TNEIVTLNYLEPRTEYELCVQLVRRGEGGEGHPGPVRRFTTA  539
     .|   |  | ..|  |||   |  |:|:|.:  |||  |.||||||  ||.  :||.
 492 DWSTIVVDPSENVTLMNLRPKTGYSVRVQLSRPGEGGEGAWGPPTLMTTD  541

540 SIG.LPPPRGLNLLPKSQTTLNLTW.QPIFPSS..EDDFYVEVERRSVQK  585
     : :  |  .|:   .:  ..:  ..|..:.|   |:..|:.   :|:|.: :    ...
 542 CPEPLLQPWLEGWHEVGTDRLRVSWSLPLVPGPLVGDGFLLRLWDGTRGQ  591

586 SDQQNIKVPGNLTSVLLNNLEPREQYVVRARVNTKAQGEWSEDLTAWTLS  635
     .  .:|:.  |..  |.  ||..|  |  .:|  :   ..:   .   :  ...  .      |.
 592 ERRENVSSPQARTA.LLTGLTPGTHYQLDVQLYHCTLLGPASPPAHVLLP  640

636 DILPPQPENIKISNITHSSAVISWTILDGY..SISSITIRYKVQGKNEDQ  683
     .   ||.|   ::.    .:..|.   :.|.  ::.   .||...:   .|.|  .:|.
 641 PSGPPAPREHLAQALSDSEIQLTWKHPEALPGPISKYVVEVQVAGGAGDP  690

684 ...HVDVKIKNATIIQYQLKGLEPETAY......QVDIFAENNIGSSNPA  724
     .||  .  ...|||         :||::.|  |         ::  :::  . .  .:..
 691 LWIDVDRPEETSTII....RGLNASTRYLFRMRASIQGLGDWSNTVEEST  736

725 FSHEL...VTLPESQAPADLGGGKMLLIAILGSAGMTCLTVLLAFLIILQ  771
     ::::|     ...:.||.|  |:  |  |'.  |::|::||.:  ||||:|  |:|.::
 737 LGNGLQAEGPVQESRA.AEEGLDQQLILAVVGSVSATCLTILAALLTLVC  785

772 LKRANVQRRMAQAFQNVR.EEPAVQFNSGTLALNRKVKNNPDPTIYPVLD  820
     ::|.  ::||..  .:|...  ||.  :||.||||.|.|:.|  .|:|   |||| :
 786 IRRSCLERRRTFTYQSGSGEETILQFSSGTLTLTRRPKLQPEPLSYPVLE  835

821 WNDIKFQDVIGEGNFGQVLKARIKKDGLRMDAAIKRMKEYASKDDHRDFA  870
     |:||.|:|.|||||||||::|.||||||:|:||||.:|||||..:|||||
 836 WEDITFEDLIGEGNFGQVIRAMIKKDGLKMNAAIKMLKEYASENDERDFA  885

871 GELEVLCKLGHHPNIINLLGACEHRGYLYLAIEYAPHGNLLDFLRKSRVL  920
     ||||||||||||||||||||||.:|||||:|||||.||||||||||||||
 886 GELEVLCKLGHHPNIINLLGACKNRGYLYIAIEYAPYGNLLDFLRKSRVL  935

921 ETDPAFAIANSTASTLSSQQLLHFAADVARGMDYLSQKQFIHRDLAARNI  970
     |||||||  .::|||||||.|||:||.|.|.||:|||:||||||||||||:
 936 ETDPAFAREHGTASTLSSRQLLRFASDAANGMQYLSEKQFIHRDLAARNV  985

971 LVGENYVAKIADFGLSRGQEVYVKKTMGRLPVRWMAIESLNYSVYTTNSD  1020
     |||||...|||||||||:||||||||||||||||||||||||||||.||
 986 LVGENLASKIADFGLSRGEEVYVKKTMGRLPVRWMAIESLNYSVYTTKSD  1035

1021 VWSYGVLLWEIVSLGGTPYCGMTCAELYEKLPQGYRLEKPLNCDDEVYDL  1070
     |||:|||||||||||||||||||||||||||||:|:|.| |:|.| ||||||:|
1036 VWSFGVLLWEIVSLGGTPYCGMTCAELYEKLPQADRMEQPRNCDDEVYEL  1085

1071 MRQCWREKPYERPSFAQILVSLNRMLEERKTYVNTTLYEKFTYAGIDCSA  1120
     ||||||::|||||.||||.||||  :  |.||||.||.|||  .|:|.||||||..|
1086 MRQCWRDRPYERPPFAQIALQLGRMLEARKAYVNMSLFENFTYAGIDATA  1135

1121 EEAA* 1125
     |||
1136 EEA.. 1138
```

Figure 6

```
   3  VPWLGACEHRGYLYLAIEYAPHGNLLDFLRKSRVLETDPAFAIANSTASI    52 m
         ::|||||||||||||||||||||||||||||||||||||||||||||||
 886  INLLGACEHRGYLYLAIEYAPHGNLLDFLRKSRVLETDPAFAIANSTAST   935 h

53  MSSQQLLHFAADVARGMDYLSQKQFIHRDLAARNILVGENYIAKIADFGL   102 m
       ::|||||||||||||||||||||||||||||||||||||||:||||||||
 936  LSSQQLLHFAADVARGMDYLSQKQFIHRDLAARNILVGENYVAKIADFGL   985 h

103  SRGQEVYVKKTMGRLPVRWMAIESLNYSVYTTNSDVWSYGVLLWEIVSLG   152 m
      ||||||||||||||||||||||||||||||||||||||||||||||||||
 986  SRGQEVYVKKTMGRLPVRWMAIESLNYSVYTTNSDVWSYGVLLWEIVSLG  1035 h

153  GTPYCGMTCAELYEKLPQGYRLEKPLNCDDEVYDLMRQCWREKPYERPSF   202 m
      ||||||||||||||||||||||||||||||||||||||||||||||||||
1036  GTPYCGMTCAELYEKLPQGYRLEKPLNCDDEVYDLMRQCWREKPYERPSF  1085 h

203  AQILVSLNRMLEERKTYVNTTLYEKFTYAGIDCSAEEAA    241 m
      |||||||||||||||||||||||||||||||||||||||
1086  AQILVSLNRMLEERKTYVNTTLYEKFTYAGIDCSAEEAA   1124 h
```

TYROSINE KINASE

CROSS-REFERENCE TO RELATED APPLICATION

This application is a continuation of U.S. application Ser. No. 07/905,600, filed Jun. 26, 1992, abandoned.

BACKGROUND

The ability of cells to respond to environmental cues is in large part due to the interaction of cell-surface receptors with external stimuli. A number of factors that interact with receptors have been identified, among which are receptor-binding proteins that are soluble, membrane-bound, or exist in both forms.

One class of receptors, the receptor tyrosine kinases (RTKs), has been intensively studied and shown to be crucial to the growth and differentiation of a variety of cell types (Yarden and Ullrich, Ann. Rev. Biochem. 57:433–478, 1988). Tyrosine kinases are enzymes that catalyze the phosphorylation of tyrosine residues. Tyrosine phosphorylation is associated with signal-transduction across the cellular plasma membrane. The protein-tyrosine kinase family can be grouped into two very broad families: the above-mentioned RTKs, which are, or are intimately associated with, membrane-spanning growth factor receptors; and those that are associated with the membrane but lack a transmembrane sequence (Yarden and Ullrich, 1988, supra.).

The RTKs can be further divided into five subgroups on the basis of structural similarities in their extracellular domains and the organization of the tyrosine kinase catalytic region in their cytoplasmic domains. Subgroups I (epidermal growth factor (EGF) receptor-like), II (insulin receptor-like) and the eph/eck family contain cysteine-rich sequences (Hirai et al., Science 238:1717–1720, 1987; Yanden and Ullrich, Ann. Rev. Biochem, 57,443–478, 1988; Lindberg and Hunter, Mol. Cell. Biol.. 10:6316–6324, 1990). The functional domains of the kinase region of these three classes of RTKs are encoded as a contiguous sequence (Hanks et al., Science 241, 42–52, 1988). Subgroups III (platelet-derived growth factor (PDGF) receptor-like) and IV (the fibroblast growth factor (FGF) receptors) are characterized as having immunoglobulin (Ig)-like folds in their extracellular domains, as well as having their kinase domains divided in two parts by a variable stretch of unrelated amino acids (Yanden and Ullrich, 1988; Hanks et al., 1988).

While all members of the RTK family share a related cytoplasmic catalytic domain, the extracellular, ligand-binding domains of these receptors have adapted patchwork structure utilizing several structural motifs. The variablility in the structure of the ligand-binding domains of the RTKs almost certainly reflects the diversity of the ligands for these receptors (Ullrich and Schlessinger, Cell 61,203–212, 1990). These ligands range from relatively small, soluble peptides to cell-surface proteins that themselves resemble receptors. Examples of ligands bound by certain members of the RTK family are polypeptide growth factors and hormones.

To deal with this diversity of ligands the RTKs have evolved extracellular domains that are a composite of several structural motifs. For example, the extracellular domain of the axl/ark gene contains both Ig-domains and fibronectin type III (FNIII) repeats (O'bryan et al., Mol. Cell. Biol. 11:5016–5031, 1991; Rescigno et al., Oncogene 6:1909–1913, 1991), while members of the eph family have those two motifs separated by a (non-EGF-like) cysteine-rich domain (Hirai et al., Science 238:17 17–1720, 1987; Lindberg et al., Mol. Cell. Biol. 10:6316–6324, 1990; Lhotak et al., Mol. Cell. Biol. 11:2496–2502, 1991; Chan and Watt, Oncogene 6:1057–1061,1991). This diversity strongly suggests that this family of receptors evolved by accumulating the structural motifs needed for ligand binding and combining these motifs with a conserved catalytic don-min.

In view of the role tyrosine kinases play in cell growth and differentiation, as well as signal transduction, isolation of novel tyrosine kinases enables one to study such biological processes. Identifying tyrosine kinases and their ligands also permits exploration of methods for inhibiting or enhancing the interaction thereof, depending on the desired biological effect.

SUMMARY OF INVENTION

The present invention provides a novel receptor (a protein tyrosine kinase), isolated DNA encoding the tyrosine kinase, recombinant expression vectors containing the isolated DNA, and host cells transformed with the recombinant vector. Also provided is a method for producing the novel protein by cultivating the transformed host cells under conditions that promote expression of the tyrosine kinase, and recovering the expressed tyrosine kinase.

BRIEF DESCRIPTION OF FIGURES

FIG. 1 presents a nucleotide sequence and deduced amino acid sequence of human ork cDNA. The nucleotide sequence is derived from two overlapping cDNA clones isolated from placental cDNA libraries. The initiating methionine codon and the transmembrane region are each underlined. The two cysteines of the inmmunoglobulin domain are boxed, as are the three EGF-like repeats. Brackets enclose the region amplified by PCR using primers based on conserved kinase domain sequences, as described in example 1. Numbering of nucleotides is in the left margin, while numbering of amino acids is on the right. The signal peptide comprises amino acids 1–18, with the threonine residue at position 19 being the first amino acid of the mature protein. The extracellular domain comprises amino acids 19–745, and the cytoplasmic domain comprises amino acids 773–1124.

FIG. 2 presents an analysis of the EGF repeats in the ork sequence. The three EGF-repeats in the ork sequence were aligned with are another. The conserved cysteine residues are boxed.

Figure 3B:
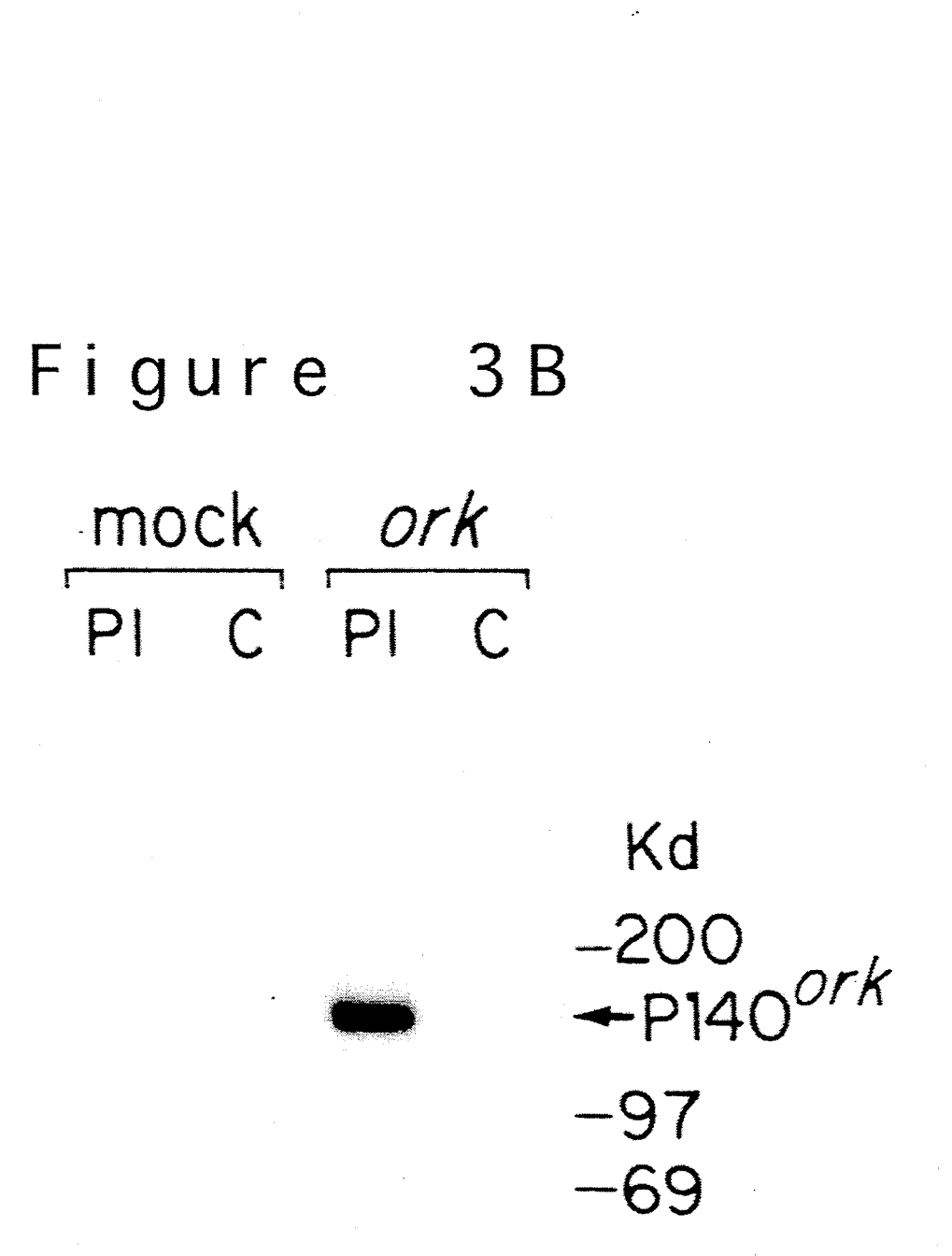

FIGS. 3A, 3B, 3C and 3D present the results of studies described in example 2 below. The human ork cDNA encodes a 140 Kd phosphoprotein with in vitro tyrosine kinase activity. 3A. COS cells were transfected with the ork cDNA (ork), or a control plasmid without cDNA insert (mock), metabolically labelled with $^{35}$S-met/cys, and immunoprecipitated with the P1 rabbit antiserum, raised against the carboxy-terminal 21 amino acids of the predicted ork amino acid sequence (P1 ), or with pre-immune serum (C). The position of P140$^{ork}$ is indicated, its are the positions of size standards. 3B. COS cells were transfected and immunoprecipitated as described above. The immunoprecipitates were incubated with $^{32}$P-ATP and separated by SDS-PAGE. The positions of P140$^{ork}$ and size standards are indicated. 3C. The gel from Panel B was transferred to a membrane, exposed to X-ray film and the band corresponding to P140^ork was excised. The filter slice was boiled in 6N HCl and eluted material was separated by two-dimensional electrophoresis. The positions of standards for phosphoserine, phosphothreonine and phosphotyrosine, as well as the origin, are indicated. 3D. COS cells were transfected and immunoprecipitated as described above. The immunoprecipitates were separated by SDS-PAGE, transferred to a membrane and incubated with an anti-phosphotyrosine antibody. The positions of size standards are indicated.

FIGS. 5a and 5b depict a comparison of tile amino acid sequences of ork (top lines) and tie (bottom lines), the latter being a tyrosine kinase of the same subgroup as ork. The sequence comparison was generated by the GAP computer program described. Identical amino acids are indicated with a line: conservative or similar amino acid changes are indicated with two dots or one dot, respectively. The percent similarity and percent identity for the ork and tie sequences were found to be 64.5% and 47.5%, respectively.

FIG. 6 presents a comparison of the amino acid sequence encoded by a murine ork clone with the corresponding portion of a human ork protein.

DETAILED DESCRIPTION OF INVENTION

Figure 3A:
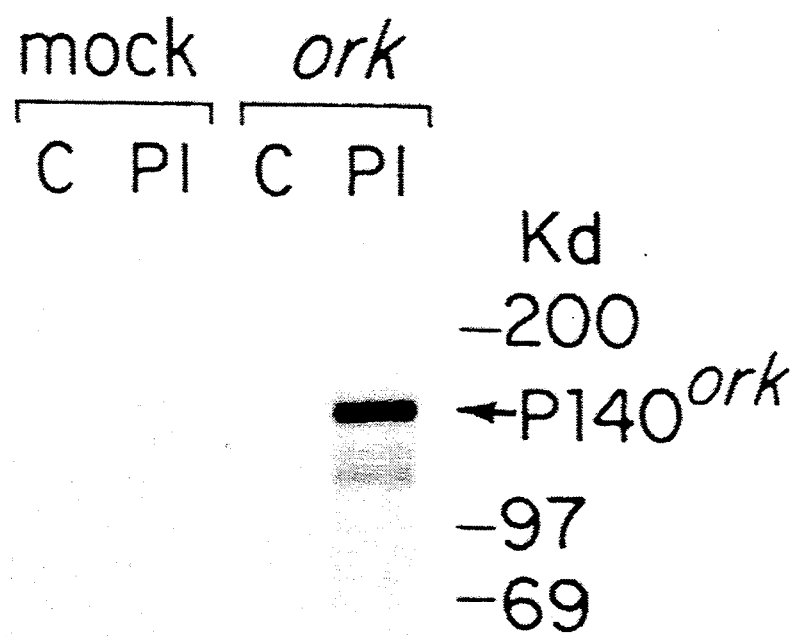

The present invention provides a novel receptor protein tyrosine kinase, isolated DNA encoding the tyrosine kinase, recombinant expression vectors containing the isolated DNA, and host cells transformed with the recombinant vector. A method for producing the novel protein involves cultivating the transformed host cells under conditions that promote expression of the tyrosine kinase, and recovering the expressed tyrosine kinase from the cell culture.

The novel protein is designated herein as ork (orphan receptor tyrosine kinase). An ork cDNA isolated from human placenta and transfected into COS-7 cells encodes a 140 Kd protein with the following combination of structural motifs in its extracellular domain: an immunoglobulin (Ig)-like domain followed by three epidermal growth factor (EGF)-like cysteine-rich repeats, which in turn are followed by three fibronectin type III (FNIII) repeats. Of the human tissues tested (example 3 below), the ork gene is expressed predominately in placenta and lung, with lower levels in umbilical vein endothelial cells, brain and kidney.

Human ork is within the scope of the present invention, as are ork proteins derived from other mammalian species. As used herein, the term "ork" includes membrane-bound proteins (comprising a cytoplasmic domain, a transmembrane region, and an extracellular domain) as well as truncated proteins that retain the desired biological properties. Such truncated proteins include, for example, soluble ork comprising only the extracellular (ligand binding) domain.

Using a polymerase chain reaction-based approach we have isolated ork cDNA and characterized this novel receptor protein tyrosine kinase. As described in example 1 below, degenerate oligonucleotide probes based on certain sequences that are conserved within the kinase domain of RTKs were used as primers in a PCR reaction. Single-stranded cDNA derived from human placental poly(A)+RNA was employed as the template. The PCR reaction products were inserted into a cloning vector and the nucleotide sequence of the cDNA inserts in a number of the resulting recombinant vectors was determined. A clone containing a cDNA insert of about 200 basepairs with a novel DNA sequence was identified.

The cDNA insert was excised, radiolabeled, and used to probe an oligo-dT-primed human placental cDNA library. A hybridizing clone comprising a 2.3 Kb insert was identified, sequenced, and found to be a partial clone encoding a C-terminal ork fragment. The cDNA insert was excised, radiolabeled, and used to probe a random-primed human placental cDNA library. A clone comprising a cDNA insert about 4.0 Kb in length that contained an entire coding region for the novel protein, as well as 5' and 3' untranslated sequences, was isolated. The 4.0 kb ork cDNA in plasmid pBLUESCRIPT®SK in E. coli strain DH5α was deposited with the American Type Culture collection on May 28, 1992 and was given accession number ATCC 69003. The strain deposit was made under the terms of the Budapest Treaty.

A DNA sequence for a human ork cDNA is presented in FIG. 1, along with the amino acid sequence encoded thereby. Several Human ork DNA and amino acid sequences identical to those of FIG. 1 are presented in SEQ ID NO: 1 and SEQ ID NO: 2 features of the ork amino acid sequence are noteworthy. The extracellular domain is a patchwork of three structural motifs. Between amino acid residues 211 and 340 are three copies of an EGF-like cysteine repeat (Davis, *New Biologist* 2:410–419, 1991). The EGF-like repeats in the ork gene (boxed in FIG. 1) differ from the consensus motif in that they have 8 cysteines each instead of 6. In this regard they are closely related to those in the tie gene (Partanen et al., *Mol. Cell. Biol.*, 12:1698–1707, 1992). The proteins with the next most closely related cysteine repeats are laminin B1, laminin B2 (Sasaki et al., *J. Biol. Chem* 263:16536–16544, 1988) and TAN, the human homolog of the Drosophila notch gene (Ellison et al, *Cell* 66:649–661). The three EGF-repeats in the ork sequence were aligned in FIG. 2. In each case the cysteines in the repeat were aligned. The three extracellular domains aligned in FIG. 2 comprise amino acids 211–251, 255–298, and 302–340, respectively, of SEQ ID NO: 2.

Amino terminal to the EGF repeats are paired cysteines (boxed in FIG. 1) indicative of Ig-like domains. This Ig domain is most similar to the C2 type as described by Williams and Barclay, *Ann. Rev. Immunol.* 6:381–405, 1988. A second pair of cysteine residues follow the EGF repeats: however the additional amino acid residues required to generate a proper Ig-fold are missing. At the membrane proximal region of the extracellular domain, between amino acids 440 and 733, are three repeats of the fibronectin type III motif. Thus, the extracellular domain of ork is a structural mosaic consisting of repeats of at least three different functional motifs.

Amino acid residues 746–772 are hydrophobic in nature and likely serve as a transmembrane domain. The cytoplasmic domain contains all the amino acid sequence hallmarks of a tyrosine kinase (I-tanks et at., *Science* 241:42–52, 1988). A comparison of the ork amino acid sequence with known protein tyrosine kinases showed ork to be a member of the RTK family.

Within the receptor tyrosine kinase family, the ork and above-mentioned tie genes form their own subgroup. The tie gene (described by Partanen et al., supra) has an extracellular domain that, like ork, comprises (from N- to C-terminus) an Ig-like domain followed by three EGF-like domains, an incomplete Ig-like domain, and three fibronectin type III repeats next to the transmembrane region. Additionally, a cDNA form lacking the first of the three epidermal growth factor homology domains was isolated by Partanen et al., supra, suggesting that alternative splicing creates different tie-type receptors. COS-7 cells transfected with a tie cDNA expression vector produced a glycosylated protein of 117 kDa.

A comparison of the amino acid sequences of ork and tie is presented in FIGS. 5a and 5b, which shows them to be distinct proteins. The tie amino acid sequence in FIGS. 5a and 5b is also presented in SEQ ID NO: 8. The comparison presented in FIGS. 5a and 5b was generated using the GAP computer program, which is described in detail below. The percent similarity and percent identity of the ork and tie amino acid sequences was found to be 64.5% and 47.5%, respectively. The RTK subgroup containing ork and tie is characterized by a unique arrangement of structural motifs in the proteins' extracellular domain, as described above. There are also several features in the cytoplasmic kinase domain worth noting. There is a short amino acid insert between the two pans of the kinase domains (FIG. 1). This insert is similar in size to that seen in the ret gene (Takahashi and Cooper, Mol. Cell. Biol. 7:1378–1385, 1987). However, unlike the insert sequences in other RTK subgroups, the insert in the ork and tie genes contains no tyrosine residues. Several tyrosine residues are found in tile cytoplasmic tail. As phosphorylation of tyrosine in either the kinase insert or tile cytoplasmic rail is required for association of the RTK molecule with putative signal transduction molecules, this feature of the ork and tie genes mostly closely resembles the EGFR subfamily where phosphorylated tyrosine residues in the cytoplasmic tail have been shown to associate with other proteins such as phospholipase C-γ,(Margolis et al., Cell 57:1101–1107, 1989).

One embodiment of the present invention provides an ork protein comprising an extracellular domain that comprises (from N- to C-terminus) an immunoglobulin-like domain, three EGF-like cysteine-rich repeats, and three FNIII repeats, wherein the amino acid sequence of said extracellular domain is at least 80% identical to the sequence shown as amino acids 19–745 of (SEQ ID NO: 1). The extracellular domain amino acid sequence preferably is at least 90% identical to the extracellular domain sequence of (SEQ ID NO: 1). The percent identity between two amino acid sequences may be determined by using the GAP computer program available from the University of Wisconsin and described in detail below. Such ork proteins include those having a transmembrane region and a cytoplasmic domain (or a portion thereof) in addition to the extracellular domain. Such proteins also include those in which a sequence containing a pair of cysteines is positioned between the last EGF-like repeat and the first FN III repeat. Such a sequence (a stretch of amino acids resembling an incomplete Ig-like domain) is found in the native human ork protein described above. Since this sequence is not believed to function as an Ig-like domain, it is possible that ork proteins lacking some or all of this partial Ig-like domain (amino acids 341–439) will retain the ability to bind a ligand. The ork proteins when initially synthesized may comprise a signal peptide as well.

The expression pattern of the ork gene suggests that it is predominately expressed in endothelial cells. The structure of the extracellular domain, with the three EGF repeats, is especially intriguing in light of this. Several cell adhesion molecules, including endothelial-leukocyte adhesion molecule-1 (ELAM-1) contain EGF repeats. ELAM-1 is expressed on tile surface of activated endothelial cells and is involved in the attachment of neutrophils at sites of inflammation (Bevilacqua et al., Science 243:1150–1165, 1989; Siegelman et al., Cell 61:611–622, 1990). Several adhesion molecules also contain Ig and FNIII repeats as well. This suggests a possible role for tile ork gene product in the communication between endothelial cells and leukocytes at sites of inflammation.

cDNA encoding an ork polypeptide may be isolated from other mammalian species by procedures analogous to those employed in isolating the human ork clone. For example, a cDNA library derived from another mammalian species may be substituted for the human cDNA library that was screened using the degenerate probes in example 1 below. Alternatively (and preferably), the human ork cDNAs isolated in example 1 are labeled and used as probes to screen mammalian cDNA or genomic libraries using crossspecies hybridization techniques. The probe may be derived from the coding region of the above-described 2.3 kb or 4.0 kb human ork cDNAs.

Murine ork cDNA was identified by cross-species hybridization. A murine cDNA library was screened using the 2.3 Kb human ork cDNA as a probe, as described in example 5.

Cell types from which cDNA and genomic libraries may be prepared include those in which ork RNA expression was detected in example 3. mRNAs isolated from various cell lines can be screened by Northern hybridization to determine additional suitable sources of mammalian ork mRNA for use in cloning an ork gene. Nucleic acid from mammalian sources that include but are not limited to murine, bovine, porcine, and primate, may be screened to identify ork genes.

In addition to the membrane-bound full length protein depicted in (SEQ ID NO: 16), the present invention provides soluble forms of the ork protein. "Soluble ork" as used in the context of the present invention refers to polypeptides that contain all or part of the extracellular region of a native ork and that, due to the absence of a transmembrane region that would cause retention of the polypeptide on a cell membrane, are secreted upon expression. Fragments of the extracellular domain may be employed as long as the fragment possesses the desired biological activity (e.g., binding to an anti-ork antibody or to the ligand for ork). Soluble ork may also include part of the transmembrane region or part of the cytoplasmic domain or other sequences, provided that the soluble ork protein is capable of being secreted. Preferred soluble ork polypeptides include the signal sequence and entire extracellular domain (amino acids 1 to 745 of SEQ ID NO: 1) or lack the signal sequence but contain the entire extracellular domain (amino acids 19 to 745 of (SEQ ID NO: 1).

Soluble ork polypeptides may be identified (and distinguished from their non-soluble membrane-bound counterparts) by separating intact cells which express the protein in question from the culture medium, e.g., by centrifugation, and assaying the medium (supernatant) for the presence of ork. The presence of ork in the medium indicates that the protein was secreted from the cells and thus is a soluble form. Soluble ork may be naturally-occurring forms of these proteins, such as those resulting from alternative splicing events. Alternatively, soluble fragments of ork proteins may be produced by recombinant DNA technology or otherwise isolated, as described below.

The use of soluble forms of ork is advantageous for certain applications. Purification of the proteins from recombinant host cells is facilitated, since the soluble proteins are secreted from the cells. The smaller soluble fragments may be advantageous for use in certain in vitro assays. The soluble ork polypeptides may be employed to competitively bind the ligand in vivo, thus inhibiting signal transduction activity via endogenous cell surface bound ork proteins. Further, soluble proteins are generally more suitable for intravenous administration and may exert their desired effect (e.g., binding a ligand) in the bloodstream.

Truncated ork proteins, including soluble polypeptides, may be prepared by any of a number of conventional techniques. In the case of recombinant proteins, a DNA fragment encoding a desired ork fragment may be subcloned into an expression vector. A desired DNA sequence may be chemically synthesized using known techniques. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein.

In another approach, enzymatic treatment (e.g., using Bal 31 exonuclease) may be employed to delete terminal nucleotides from a DNA fragment to obtain a fragment having a particular desired terminus. Among the commercially available linkers are those that can be ligated to the blunt ends produced by Bal 31 digestion, and which contain restriction endonuclease cleavage site(s). Alternatively, oligonucleotides that reconstruct the N- or C-terminus of a DNA fragment to a desired point may be synthesized. The oligonucleotide may contain a restriction endonuclease cleavage site upstream of the desired coding sequence and position an initiation codon (ATG) at the N-terminus of the coding sequence.

The well known polymerase chain reaction procedure also may be employed to amplify a DNA sequence encoding a desired protein fragment. 3' and 5' oligonucleotide primers that anneal to the ork DNA at the termini of a desired fragment are employed in the PCR reaction which is conducted using any suitable procedure, such as those described in Sarki et al., *Science* 239:487 (1988); in *Recombinant DNA Methodology*, Wu et al., eds., Academic Press Inc., San Diego (1989), pp. 189–196; and in *PCR Protocols: A Guide to Methods anti Applications*, Innis et al., eds., Academic Press, Inc. (1990). An example of a suitable PCR procedure is as follows. All temperatures are in degrees centigrade. The following PCR reagents are added to a 0.5 ml Eppendorf microfuge tube: 10 μl of 10X PCR buffer (500 mM KCl, 100 mM Tris-HCl, pH 8.3 at 25° C., 25 mM MgCl$_2$, and 1 mg/ml gelatin) (Perkin-Elmer Cetus, Norwalk, Conn.), 8 μl of a 2.5 mM solution containing each dNTP (2 mM dATP, 2 mM dCTP, 2 mM dGTP and 2 mM dTTP), 2.5 units (0.5 μl of standard 5000 units/ml solution) of Taq DNA polymerase (Perkins-Elmer Cetus), 1 ng of template DNA, 100 picomoles of each of the oligonucleotide primers, and water to a final volume of 100 μl. The final mixture is then overlaid with 100 μl parafin oil. PCR is carried out using a DNA thermal cycler (Ericomp, San Diego, Calif.). The template is denatured at 94° for 5 minutes and PCR is carried out for 25 cycles of amplification using a step program (denaturation at 94°, 1.5 minutes; annealing at 60°, 1 minute; extension at 72°, 1 minute).

The present invention also provides full length ork protein or antigenic fragments thereof that can act as immunogens to generate antibodies specific to the ork immunogens. Monoclonal antibodies specific for ork or antigenic fragments thereof are prepared by prodedures that include those described in Example 4. The above-described procedures for producing ork fragments may be employed in producing ork fragments for use as immunogens.

Expression of Recombinant ork Proteins

The present invention provides recombinant expression vectors to express DNA encoding the ork proteins of the present invention. The inventive recombinant expression vectors are replicable DNA constructs which contain a synthetic or cDNA-derived DNA sequence encoding an ork protein, operably linked to suitable transcriptional or translational regulatory elements. Examples of genetic elements having a regulatory role in gene expression include transcriptional promoters, operators or enhancers, a sequence encoding suitable mRNA ribosomal binding sites, and appropriate transcription and translation initiation and termination sequences. The ability to replicate in a host, usually conferred by an origin of replication, and a selection gene to facilitate recognition of transformants may additionally be incorporated. The regulatory elements employed in the expression vectors are generally derived from mammalian, microbial, vital, or insect genes. Expression vectors derived from retroviruses also may be employed.

DNA regions are operably linked when they are functionally related to each other. A DNA sequence encoding ork is said to be operably linked to one or more of the above-described regulatory elements when the ork DNA sequence is transcribed, or the resulting mRNA is translated, under the control of the regulatory element(s).

Transformed host cells are cells which have been transformed or transfected with foreign DNA using recombinant DNA techniques. In the context of the present invention, the foreign DNA includes a sequence encoding the inventive ork protein. Host cells may be transformed for purposes of cloning or amplifying the foreign DNA, or may be transformed with an expression vector for production of the fusion protein under the control of appropriate promoters. Suitable host cells include prokaryotes, yeast, or higher eukaryotic cells. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosures of which is hereby incorporated by reference. Cell-free translation systems could also be employed to produce fusion protein using RNAs derived from the DNA constructs of the present invention.

Prokaryotes include gram negative or gram positive organisms. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Examples of suitable prokaryotic hosts for transformation include *E. coli*, bacilli such as *Bacillus subtilis, Salmonella typhimurium*, and various species within the genera Pseudomonas, Streptomyces, and Staphylococcus, although others may also be employed as a matter of choice.

Useful expression vectors for bacterial use can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance, providing simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* . 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and cI857ts thermoinducible repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

The recombinant ork protein may also be expressed in yeast hosts, preferably from Saccharomyces species, such as *S. cerevisiae*. Yeast of other genera such as Pichia or Kluyveromyces may also be employed. Yeast vectors will generally contain an origin of replication from the 2 μm yeast plasmid or an autonomously replicating sequence (ARS), a promoter, DNA encoding the ork protein, sequences for polyadenylation and transcription termination and a selection gene. Yeast vectors may include origins of replication and selectable markers permitting transformation of both yeast and *E. coli*, e.g., the ampicillin resistance gene of *E. coli* and the *S. cerevisiae* trp1 gene. The trp 1 gene provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* . 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Examples of suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al., (*Nature* 300:724, 1982). Advantageously, a DNA segment encoding a leader sequence functional in yeast is operably linked to the 5' end of the DNA encoding the ork protein. The encoded leader peptide promotes secretion of the ork protein from the host cell and is generally cleaved from the ork protein upon secretion. As one example, the yeast α-factor leader, which directs secretion of heterologous proteins, can be inserted between the promoter and the structural gene to be expressed. See, e.g., Kurjan et al., *Cell* 30:922, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

Suitable yeast transformation protocols are known to those of skill in the art. An exemplary technique is described by Hinnen et al., *Proc. Natl. Acad. Sci. USA* 75: 1929, (1978), selecting for Trp+ transformants in a selective medium consisting of 0.67% yeast nitrogen base, 0.5% casamino acids, 2% glucose, 10 μg/ml adenine and 20 μg/ml uracil. Host strains transformed by vectors comprising the above-described ADH2 promoter may be grown or expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Established cell lines of mammalian origin may be employed. Examples of suitable mammalian host cell lines include the COS-7 line of monkey kidney cells (ATCC CRL 1651), described by Gluzman (*Cell* 23:175, 1981), CV-1 cells (ATCC CCL 70) also derived from monkey kidney, L cells, C127, 3T3, Chinese hamster ovary (CHO), HeLa and BHK cell lines. Mammalian expression vectors may comprise non-transcribed elements such as an origin of replication, a suitable promoter and enhancer linked to the gene to be expressed, and other 5' or 3' flanking non-transcribed sequences, and 5' or 3' nontranslated sequences, such as necessary ribosome binding sites, a poly-adenylation site, splice donor and acceptor sites, and transcriptional termination sequences.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 vital origin or replication (Fiers et al., *Nature* 273:113, 1978). Smaller or larger SV40 fragments may also be used, provided the approximately 250 bp sequence extending from the Hind III site toward the BglI site located in the vital origin of replication is included. Exemplary vectors can be constructed as disclosed by Okayama and Berg (*Mol. Cell. Biol.* 3:280, 1983). A useful system for stable high level expression of mammalian receptor cDNAs in C127 murine mammary epithelial cells can be constructed substantially as described by Cosman et al. (*Mol. Immunol.* 23:935, 1986). Other expression vectors for use in mammalian host cells are derived from retroviruses.

Producing and Purifying the ork Protein

The present invention provides substantially homogeneous ork protein, which may be produced by recombinant expression systems as described above or purified from naturally occurring cells. The ork protein is purified to substantial homogeneity, as indicated by a single protein band upon analysis by SDS-polyacrylamide gel electrophoresis (SDS-PAGE).

In one embodiment of the present invention, ork is purified from a cellular source using any suitable protein purification technique. The tissues identified in example 3 as containing ork RNA (preferably placental or lung tissue) from a mammalian species of interest may be employed as sources of ork, for example.

An alternative process for producing the recombinant ork protein of the present invention comprises culturing a host cell transformed with an expression vector comprising a DNA sequence that encodes said ork protein under conditions that promote expression of the ork protein, which is then purified from culture media or cell extracts. Any suitable purification process may be employed, with the procedure of choice varying according to such factors as the type of host cells and whether or not the desired protein is secreted from the host cells. The fusion protein will be secreted into the culture medium when it is initially fused to a signal sequence or leader peptide operative in the host cells, or when the protein comprises soluble forms of the ork polypeptides.

For example, supernatants from expression systems which secrete recombinant protein into the culture medium can be first concentrated using a commercially available protein concentration filter, e.g., an Amicon or Millipore Pellicon ultrafiltration unit. Following the concentration step, the concentrate can be applied to a suitable purification matrix. For example, an immunoaffinity column comprising antibodies directed against ork and bound to a suitable support may be employed. A monoclonal antibody specific for ork may be prepared as described in example 4. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. One or more reversed-phase high performance liquid chromatography (RP-HPLC) steps employing hydrophobic RP-HPLC media, e.g., silica gel having pendant methyl or other aliphatic groups, can be employed to further purify ork.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant fusion proteins can disrupted by any convenient method, including freeze-thaw cycling, sonication, mechanical disruption, or use of cell lysing agents.

Fermentation of yeast which express ork as a secreted protein greatly simplifies purification. Secreted recombinant protein resulting from a large-scale fermentation can be purified by methods analogous to those disclosed b), Urdal et al. (*J. Chromatog.* 296:171, 1984), involving two sequential, reversed-phase HPLC steps for purification of a recombinant protein on a preparative HPLC column.

Some or all of the foregoing purification steps, in various combinations, can be employed to provide an essentially homogeneous recombinant protein. Recombinant cell culture enables the production of the ork protein free of those contaminating proteins which may be normally associated with ork as it is found in nature, e.g., in cells, cell exudates or body fluids. The foregoing purification procedures are among those that may be employed to purify non-recombinant ork proteins of the present invention as well.

Variants and Derivatives of ork

Variants and derivatives of native ork proteins that retain the desired biological activity am also within the scope of the present invention. An ork variant, as referred to herein, is a polypeptide substantially homologous to a native ork, but which has an amino acid sequence different from that of native ork (human, murine or other mammalian species) because of one or a plurality of deletions, insertions or substitutions.

The variant amino acid sequence preferably is at least 80% identical to a native ork amino acid sequence, most preferably at least 90% identical. When the variant ork protein comprises extracellular, transmembrane and cytoplasmic domains, these percent identities apply to the entire sequence and also to the extracellular domain when taken alone. Since the cytoplasmic domains are relatively conserved among members of the RTK family, the percent identity of the extracellular domain is important in identifying a variant as an ork protein.

To illustrate this point, a comparison of the full length ork and tie amino acid sequences (aligned in FIG. 5) reveals 76% identity for the cytoplasmic domains, whereas the percent identity drops to 47.5% for the full length sequences as a whole. The percent identity drops to 33% when just the extracellular domains are compared. A DNA probe corresponding to the extracellular region of tie would not hybridize to ork DNA under moderately stringent hybridization conditions.

The degree of homology (percent identity) may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Briefly, the GAP program defines similarity as the number of aligned symbols (i.e., nucleotides or amino acids) which are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and all additional 0.10 penalty for each symbol in each gap; and (3) no penalty for end gaps.

Alterations of the native amino acid sequence may be accomplished by any of a number of known techniques. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering:Principles and Methods*, Plenum Press, 1981); and U.S. Pat. Nos. 4,518,584 and 4,737,462, which are incorporated by reference herein.

Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; GLu and Asp; or Gln and Asn. Other such conservative substitutions, for example, substitutions of entire regions having similar hydrophobicity characteristics, are well known.

ork also may be modified to create ork derivatives by forming covalent or aggregative conjugates with other chemical moieties, such as glycosyl groups, lipids, phosphate, acetyl groups and the like. Covalent derivatives of ork may be prepared by linking the chemical moieties to functional groups on ork amino acid side chains or at the N-terminus or C-terminus of an ork polypeptide or the extracellular domain thereof. Other derivatives of ork within the scope of this invention include covalent or aggregative conjugates of ork or its fragments with other proteins or polypeptides, such as by synthesis in recombinant culture its N-terminal or C-terminal fusions. For example, the conjugate may comprise a heterologous signal or leader polypeptide sequence at the N-terminus of an ork polypeptide. Examples of such signal peptides are the α-factor leader of Saccharomyces; the signal sequence for interleukin-7 (IL-7) described in U.S. Pat. No. 4,965,195; or the signal sequence for interleukin-2 receptor described in U.S. patent application Ser. No. 06/626,667 filed on Jul. 2, 1984. The signal or leader peptide co-translationally or post-translationally directs transfer of the conjugate from its site of synthesis to a site outside of the cell membrane or cell wall.

ork polypeptide fusions can comprise peptides added to facilitate purification and identification of ork. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (DYKDDDDK)(SEQ ID No: 4), which is highly antigenic and provides an epitope reversibly bound by a specific monoclonal antibody enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. A murine hybridoma designated 4E 11 produces a monoclonal antibody that binds the peptide DYKDDDDK (SEQ ID No: 4), in the presence of certain divalent metal cations (as described in U.S. Pat. No. 5,011,912) and has been deposited with the American Type Culture Collection under accession no HB 9259.

The present invention further includes ork polypeptides with or without associated native-pattern glycosylation. ork expressed in yeast or mammalian expression systems (e.g., COS-7 cells) may be similar to or significantly different from a native ork polypeptide in molecular weight and glycosylation pattern, depending upon the choice of expression system. Expression of ork polypeptides in bacterial expression systems, such as *E. coli*, provides non-glycosylated molecules.

DNA constructs that encode various additions or substitutions of amino acid residues or sequences, or deletions of terminal or internal residues or sequences not needed for biological activity or binding, can be prepared. For example, N-glycosylation sites in the ork extracellular domain can be modified to preclude glycosylation while allowing expression of a homogeneous, reduced carbohydrate analog using yeast expression systems. N-glycosylation sites in eukaryotic polypeptides are characterized by an amino acid triplet Ash-X-Y, wherein X is any amino acid except Pro and Y is Set or Thr. Appropriate modifications to the nucleotide sequence encoding this triplet will result in substitutions, additions or deletions that prevent attachment of carbohydrate residues at the Asn side chain. Known procedures for inactivating N-glycosylation sites in proteins include those described in U.S. Pat. No. 5,071,972 and EP 276,846. In another example, sequences encoding Cys residues that are not essential for biological activity can be altered to cause the Cys residues to be deleted or replaced with other amino acids, preventing formation of incorrect intramolecular disulfide bridges upon renaturation. Other variants are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein.

Naturally occurring ork variants are also encompassed by the present invention. Examples of such variants are proteins that result from alternative mRNA splicing events (since ork is encoded by a multi-exon gene) or from proteolytic cleavage of the ork protein, provided the desired biological activity (e.g., binding to an anti-ork antibody or to the ligand) is retained. Alternative splicing of mRNA may yield a truncated but biologically active ork protein, such as a naturally occurring soluble form of the protein, for example. An alternative splicing event in tie, an RTK of the same subgroup as ork, yielded a protein lacking the first of three fibronectin type III repeats. Variations attributable to proteolysis include, for example, differences in the N- or C-termini upon expression in different types of host cells, due to proteolytic removal of one or more terminal amino acids (which may occur intracellularly or during purification). Varying N-termini may also result from cleavage of the signal peptide in certain host cells at a point other than between amino acids 18 and 19 of the disclosed sequence.

In certain host cells, post-translational processing will remove the methionine residue encoded by an initiation codon, whereas the methionine residue will remain at the N-terminus of proteins produced in other host cells. The N-terminal amino acid may, for example, be any of the amino acids at positions 1 to 5 of (SEQ ID No: 1) (for proteins comprising a signal peptide) or 19–23 (for the mature protein). The C-terminus may be truncated deliberately during expression vector construction (e.g., in constructing vectors encoding soluble proteins as described above) or as a result of differential processing which may remove up to about five C-terminal amino acids, for example.

Due to the known degeneracy of the genetic code wherein more than one codon can encode the same amino acid, a DNA sequence may vary from that presented in (SEQ ID No: 1), and still encode an ork protein having the amino acid sequence of (SEQ ID No: 1). Such variant DNA sequences may result from silent mutations (e.g., occurring during PCR amplification), and may be the product of deliberate mutagenesis of a native sequence.

Nucleic acid sequences within the scope of the present invention include isolated DNA and RNA sequences that hybridize to the ork nucleotide sequences disclosed herein under conditions of moderate or severe stringency, and which encode biologically active ork. Moderate stringency hybridization conditions refer to conditions described in, for example, Sambrook et al. *Molecular Cloning: A Laboratory Manual*, 2 ed. Vol. 1, pp. 1.101–104, Cold Spring Harbor Laboratory Press, (1989). Conditions of moderate stringency, as defined by Sambrook et al., include use of a prewashing solution of 5× SSC, 0.5% SDS, 1.0 mM EDTA (pH 8.0) and hybridization conditions of about 55° C., 5× SSC, overnight. Conditions of severe stringency include higher temperatures of hybridization and washing. The skilled artisan will recognize that the temperature and wash solution salt concentration may be adjusted as necessary according to factors such as the length of the probe.

The present invention thus provides isolated DNA sequences encoding biologically active ork, selected from: (a) DNA derived from the coding region of a native mammalian ork gene (e.g., cDNA derived from the coding region of the human ork cDNA sequence presented in (SEQ ID No: 1); (b) DNA capable of hybridizing under moderately stringent conditions to a DNA derived from the extracellular region of the sequence presented in (SEQ ID No: 1), and which encodes biologically active ork; and (c) DNA which is degenerate as a result of the genetic code to a DNA defined in (a) or (b) and which encodes biologically active ork.

ork polypeptides in the form of oligomers such as dimers or trimers are within the scope of the present invention. Oligomers may be linked by disulfide bonds foraged between cysteine residues on different ork polypeptides. In one embodiment of the invention, an ork dimer is created by fusing ork to the Fc region of an antibody (IgG1). The Fc polypeptide preferably is fused to the C-terminus of a soluble ork (comprising only the extracellular domain). A gene fusion encoding the ork fusion protein is inserted into an appropriate expression vector. The ork fusion proteins are allowed to assemble much like antibody molecules, whereupon interchain disulfide bonds form between Fc polypeptides, yielding divalent ork. If fusion proteins are made with both heavy and light chains of an antibody, it is possible to form an ork oligomer with as many as four ork extracellular regions. Alternatively, one can link two soluble ork domains with a peptide linker such as the Gly$_4$SerGly$_5$Ser (SEQ ID No: 5) linker sequence described in U.S. Pat. No. 5,073,627. A fusion protein comprising two or more ork polypeptides (with or without peptide spacers) may be produced by recombinant DNA technology.

The present invention further provides antisense or sense oligonucleotides comprising a single-stranded nucleic acid sequence (either RNA or DNA) capable of binding to target ork mRNA (sense) or ork DNA (antisense) sequences. Antisense or sense oligonucleotides, according to the present invention, comprise a fragment of the coding region of ork cDNA. Such a fragment generally comprises at least about 14 nucleotides, preferably from about 14 to about 30 nucleotides. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Binding of antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block expression of ork proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oliginucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or other gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, the murine retrovirus M-MuLV, N2 (a retrovirus derived from M-MuLV), or or the double copy vectors designated DCT5A, DCT5B and DCT5C (see PCT U.S. application Ser. No. 90/02656). Alternatively, other promotor sequences may be used to express the oligonucleotide.

Sense or antisense oligonucleotides may also be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by all endogenous lipase.

Uses of Ork Proteins

One use of ork is as a research tool for identifying the ligand that binds thereto and studying the biological effects of ligand binding. The ork polypeptides of the present invention also may be employed in in vitro assays for detection of ork or its ligand or the interactions thereof.

The ork polypeptides of the present invention can be used in a binding assay to detect cells expressing a ligand for ork. For example, ork or an extracellular domain or a fragment thereof can be conjugated to a detectable moiety such as $^{125}I$. Radiolabeling with $^{125}I$ can be performed by any of several standard methodologies that yield a functional $^{125}I$ ork molecule labeled to high specific activity. Alternatively, another detectable moiety such as an enzyme that can catalyze a colorometric or fluorometric reaction, biotin or avidin may be used. Cells to be tested for ork ligand expression can be contacted with the labeled ork. After incubation, unbound labeled ork is removed and binding is measured using the detectable moiety.

Soluble ork polypeptides may be employed to competitively bind the ligand in vivo, thus inhibiting signal transduction activity via endogenous cell surface bound ork proteins. Further, soluble proteins are generally more suitable for intravenous administration and may exert their desired effect (e.g. binding a ligand) in the bloodstream. Soluble ork proteins comprising only the extracellular (ligand-binding) domain lack the tyrosine kinase domain which is located within the cytoplasmic domain.

The ork polypeptides disclosed herein are also useful in generating antibodies specific to the ork immunogens. Monoclonal antibodies specific for ork or antigenic fragments thereof may be prepared by procedures that include those described in Example 4. The monoclonal antibodies can be attached to insoluble support materials for use in immunoaffinity column purification of ork proteins. Other uses for the antibodies include detecting ork proteins in in vitro assays and identifying and purifying additional ork polypeptides such as variants (e.g., from alternative splicing events) that comprise the region from which the immunogen was derived.

EXAMPLE 1

PCR-Based Cloning of Human ork cDNA

Degenerate oligonucleotide primers were synthesized corresponding to the conserved sequences HRDLAA (TK-1; sense orientation) and SDVWS (TK-2; antisense orientation) contained within the kinase domain of all RTKs (Hanks, et al., 1988). Both oligonucleotides were 32-fold degenerate and contained recognition sequences for Xho I. The HRDLAA sequence was chosen to favor RTKs over src-family tyrosine kinases that have the sequence HRDLRA (Hanks et al., 1988).

Single-stranded cDNA was synthesized from human placental polyadenylated RNA by standard methods. The single stranded cDNA was used as template for a PCR reaction using the conditions of Wilks (1989). The two degenerate oligonucleotides were used as primers in the PCR reaction. Amplified PCR reaction products of about 200 base pairs were digested with Xho I and ligated into an Xho I-digested plasmid vector desinated pBLUESCRIPT® SK. This vector, available from Stratagene Cloning Systems, La Jolla, Calif., is replicable in *E. coil* and contains a polylinker segment that includes 21 unique restriction sites, one of which is Xho I. The ligation mixture was transformed into *E. coli* cells by conventional procedures.

Recombinant plasmids were recovered from the transformed *E. coli* cells and the nucleotide sequence of the DNA insert in a number of individual clones was determined. Among the known RTKs that were represented in the PCR-library were c-fms, JTK-4 (Partanen et al. *Proc. Natl. Acad. Sci.* USA, 87:8913–17, 1990), kdr (Terman et al., *Oncogene*, 6:1677–1683, 1991), eph (Hirai et al., 1987 supra), and flt-4 (Aprelikova et al. *Cancer Res.*, 52:746–748, 1992). However, one clone, designated HPK-6, contained a novel sequence. The approximately 200bp cDNA insert of HPK-6 was isolated and radiolabeled with $^{32}p$ by conventional techniques for use as a probe to isolate longer cDNA sequences encoding the novel protein.

An oligo-dT-primed human placental cDNA library in plasmid pDC302 has been previously described (Larsen et al., *J. Exp. Med.*, 172: 1559–1570, 1990). Briefly, total cell RNA was isolated from whole fresh placental tissue and polyadenylated RNA was prepared by chromatography on oligo (dT)-cellulose. Double-stranded, oligo(dT)-primed cDNA was prepared with a commercial kit (Amersham Corp., Arlington Heights, Ill.). The resulting cDNA was size fractionated by chromatography on Sephacryl S-1000 (Pharmacia Fine Chemicals, Piscataway, N.J.) in 0.5M sodium acetate. The excluded cDNA was cloned into the BglII site of the mammalian expresion vector, pDC302 (described below) by an adaptor method similar to that described by Haymerle et al. (*Nucl. Acids Res.* 14:8615, 1986). Briefly, noncomplementary oligonucleotides of the sequence 5'-GATCTTGGAACGAGACGACCTGCT (SEQ ID No: 6) and 5'-AGCAGGTCGTCTCGTTCCAA (SEQ ID No: 7) synthesized on a DNA synthesizer (model 380A; Applied Biosystems, Foster City, Calif.) were annealed and ligated in separate reactions to either cDNA or BglII cut vector. Nonligated oligonucleotides were separated from cDNA or vector by chromatography over Sepharose CL-2B (Pharmacia Fine Chemicals) at 65° C. in 10 mM Tris (pH 8.0), 0.1 mM EDTA. 5 ng of adaptored vector was ligated to adaptored cDNA in 10-μl reactions containing 50 mM sodium chloride, 50 mM Tris-HCl (pH 7.5), 10 mM magnesium chloride, 1 mM spermidine, 0.5 mM ATP, 0.1 U/μl T4 polynucleotide kinase and 0.4 U/μl T4 DNA ligase for 30 min at 37° C. Reactions were then desalted by drop dialysis on VSWP 013 filters (Millipore Corp., Bedford, Mass.) against distilled water for 40 min immediately before electroporation into *Escherichia coli* strain DH5a. Transformants were obtained with an average cDNA insert size of 1.6 kb.

The pDC302 expression vector employed in preparing this cDNA library has been described by Mosley et al. (*Cell* 59:335, 1989). pDC302 is an expression vector for use in mammalian host cells, but also replicates in *E. coli*.

pDC302 was assembled from pDC201 (Sims et al., *Science* 241:585, 1988), SV40 and cytomegalovirus DNA and comprises, in order with the direction of transcription from the origin of replication: (1) SV40 sequence from coordinates 5171–270 including the origin of replication, enhancer sequences and early and late promoters; (2) human cytomegalovirus sequences including the promoter and enhancer regions (nucleotides 671 to 63 from the sequence published by Boechart et al. (*Cell* 41:521, 1985); (3) adenovirus-2 sequences containing the first exon and part of the intron between the first and second. exons of the tripartite leader, the second exon and part of the third exon of the tripartite leader; and (4) a multiple cloning site (MCS) containing sites for XhoI, Asp718, SmaI, NotI and BglII; (5) SV40 sequences from coordinates 4127–4100 and 2770–2533 that include the polyadenylation and termination signals for early transcription; (6) sequences derived from pBR322 and virus-associated sequences VAI and VAII of pDC201, with adenovirus sequences 10532–11156 containing the VAI and VAII genes, followed by pBR322 sequences from 4363–2486 and 1094–375 containing the ampicillin resistance gene and origin of replication.

Miniprep DNA isolated from individual pools of colonies from the above-described placental cDNA library was digested with Bgl II (which excises the cDNA inserts) and screened for hybridization to the HPK-6-derived probe. A clone comprising a 2.3 Kb cDNA insert was isolated from one pool (#398) and the insert was radiolabeled for use in subsequent library screens.

A random-primed cDNA library in λgt10 was generated from poly(A)+ human placental RNA and screened for hybridization to the 2.3 kb cDNA probe. One clone (32-1), about 4.0 Kb in length, contained an entire coding region, as well as 5' and 3' untranslated sequences.

A DNA sequence for human ork is presented in (SEQ ID No: 1), along with the amino acid sequence encoded thereby. The (SEQ ID No: 1) sequence was derived by combining DNA sequencing information from the fully-sequenced 2.3 kb clone with that obtained for the 4.0 kb clone (for which certain portions overlapping with the 2.3 kb clone were not fully sequenced). Beginning with an ATG codon at nucleotides 149–151 there is an open reading frame extending for 1124 amino acids. Several lines of evidence suggest that this methionine codon is the initiating codon. The ATG codon is in a proper context (Kozak, 1984), and is followed by a hydrophobic stretch of amino acids that resembles a leader sequence (amino acids 1-18 of (SEQ ID No: 1), i.e., methionine through glycine). There are two in-frame termination codons upstream of the ATG codon.

The protein comprises an N-terminal extracellular (ligand-binding) domain (amino acids 19–745), followed by a transmembrane region comprising amino acids 746–772, and a C-terminal cytoplasmic domain (which contains the tyrosine kinase domain responsible for the tyrosine phosphorylating activity of the protein) comprising amino acids 773–1124.

The 2.3 kb clone encodes a C-terminal fragment of ork, including a small C-terminal portion of the extracellular domain, followed by the complete transmembrane and cytoplasmic domains of the protein (amino acids 698–1124). The 2.3 kb ork cDNA extends from nucleotide 2240 to the 3' end of the (SEQ ID No: 1) DNA sequence and contains additional 3' non-coding sequences (i.e., the 2.3 kb clone has a longer 3' non-coding region than does the 4.0 kb clone depicted in (SEQ ID No: 1)). Since the 2.3 kb clone lacks most of the extracellular domain, the tyrosine kinase encoded thereby is not expected to bind a ligand.

The 4.0 kb ork cDNA in plasmid pBLUESCRIPT®SK in *E. coil* strain DH5a was deposited with the American Type Culture collection on May 28, 1992 and was given accession number ATCC 69003. The strain deposit was made under the terms of the Budapest Treaty.

EXAMPLE 2

Characterization of ork Gene Product

Rabbit polyclonal antiserum was generated against a peptide consisting of the carboxyl-terminal 21 amino acids of the ork protein cytoplasmic domain (SEQ ID No: 1) sequence) conjugated to ovalbumin (Kitagawa and Aikawa, *J. Biochem.* 79:233-236, 1976). Animals were immunized with 100 μg of the conjugate in complete Freund's adjuvant, followed by three boosts in incomplete adjuvant, after which time test bleeds were taken and assayed for immunoreactivity towards the peptide immobilized on nitrocellulose. Bleeds that showed anti-peptide activity were used in the following immunoprecipitation experiment.

To examine the protein encoded by the ork cDNA, the full length cDNA was excised from λgt10 by Not I digestion and ligated into a Not I-digested expression plasmid pDC302 (described above). Not I cleaves pDC302 at a unique site within a multiple cloning site. The resulting recombinant vectors were transfected into COS-7 cells and 3 days later the cells were labelled with $^{35}$S-met/cys and detergent solubilized. The $^{35}$S-labeled lysates were incubated with 5 μl of the anti-peptide serum for 1 hour at 4° C., after which time 100 μl of pre-swollen proteinA-sepharose was added and the lysates were incubated for an additional hour at 4° C. The immune complexes were washed 3 times with PBS/1% Triton X-100, boiled in SDS-PAGE sample buffer, and analyzed by SDS/polyacrylamide gel electrophoresis. The gel was treated with Amplify (Amersham, Arlington Heights, Ill.) and exposed to X-Ray film.

Figure 3C:
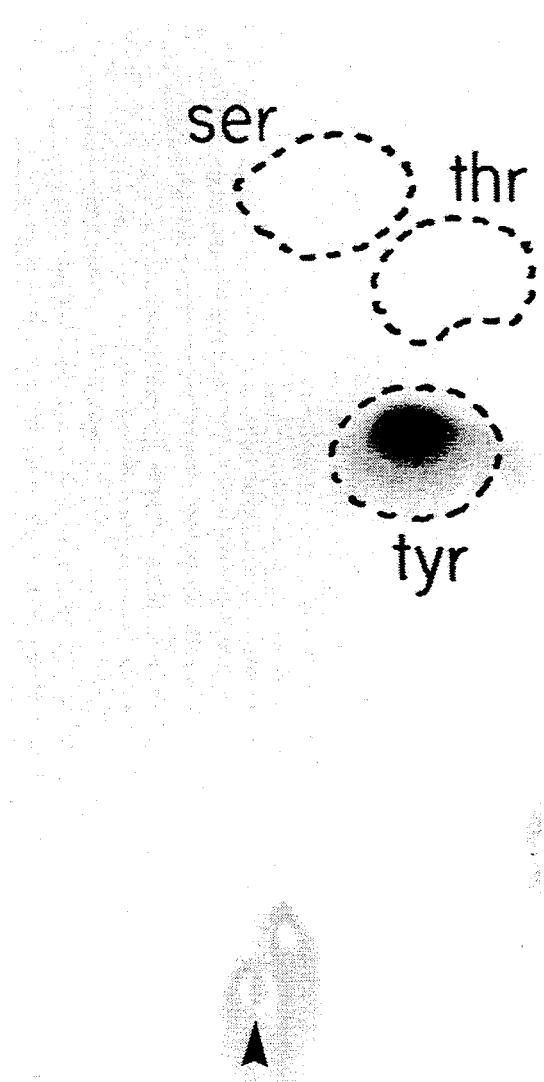
Figure 3D:

As shown in FIG. 3 (panel A), the immune serum, but not the pre-immune serum, precipitated an approximately 140 Kd protein in the lysates from the ork-transfected cells, but not in lysates from control cells. Preincubation of the immune serum with the peptide specifically blocked the precipitation of the 140 Kd protein.

A hallmark of protein tyrosine kinases is their ability to auto-phosphorylate in vitro in immune complexes (Ullrich and Schlessinger, 1990)). We tested the ability of the ork protein to autophosphorylate using the rabbit serum described above. Ork- or mock-transfected COS-7 cells were washed 1× in cold PBS/0.1 mM sodium orthovanadate and lysed at $10^7$ cells/ml in a buffer containing: 25 mM TRIS pH 8/150 mM NaCl/1 mM EGTA/1 mM DTT/1% NP-40/0.1 mM sodium orthovanadate/1 mM PMSF/10 μg/ml leupeptin/10 μg/ml pepstatin A. Lysates were incubated with 5 μl of the above-described rabbit anti-peptide serum or normal rabbit serum for 2 hours at 4° C. with 15 μl (packed volume) protein A-sepharose. Immune complexes were washed 3× with 25 mM TRIS pH 8/150 mM NaCl/1% Triton X-100/0.1% SDS/1% sodium deoxycholate/1 mM DTT/0.1 mM sodium orthovanadate/1 mM PMSF/10 μg/ml leupeptin, followed by three washes in 20 mM HEPES pH 7.4/10 mM $MnCl_2$/5 mM $MgCl_2$. In vitro phosphorylation reactions were initiated by suspending the beads to a final volume of 50 μl in a mixture containing [$\gamma^{32}$P]ATP (25 mM)/10 mM $MnCl_2$/5 mM $MgCl_2$/20 mM HEPES pH 7.4. After incubation for 30 minutes at 37° C the beads were washed with 20 mM HEPES pH 7.4/10 mM ATP/5 mM EGTA, boiled in SDS-PAGE sample buffer and separated on 8-16% SDS/polyacrylamide gels followed by autoradiography. For phosphoaminoacid analysis, separated proteins were electrophoretically transferred to membranes and regions containing $^{32}$P-labelled protein were excised and incubated with 6N HCl for 1 hour at 110° C. Hydrolysates were analysed by two dimensional thin-layer electrophoresis (Cooper et al., 1983) and autoradiography.

As shown in FIG. 3, panel B, immunoprecipitated ork was capable of auto-phosphorylation. Phosphoamino acid analysis demonstrated that only phosphotyrosine was present in the immunoprecipitates (FIG. 3, panel C). We also examined whether the ork expressed in the COS cells was phosphorylated on tyrosine residues. Lysates from ork- and control-transfected cells were immunoprecipated with the P1 (polyclonal) serum, separated by SDS-PAGE, transferred to filters and incubated with an anti-phosphotyrosine anti-serum. As shown in FIG. 3, panel D, a 140 Kd protein containing phosphotyrosine was seen only in the lysates from ork-transfected cells that had been immunoprecipitated with the anti-ork serum. It is unclear from these data whether ork has a high level of intrinsic tyrosine kinase activity, whether the COS cells express a potential ligand for ork which is interacting with the ork protein on the COS cell surface, or whether ork is being phosphorylated by a tyrosine kinase expressed by COS cells.

EXAMPLE 3

Screening Human Tissues for ork Expression

Figure 4:
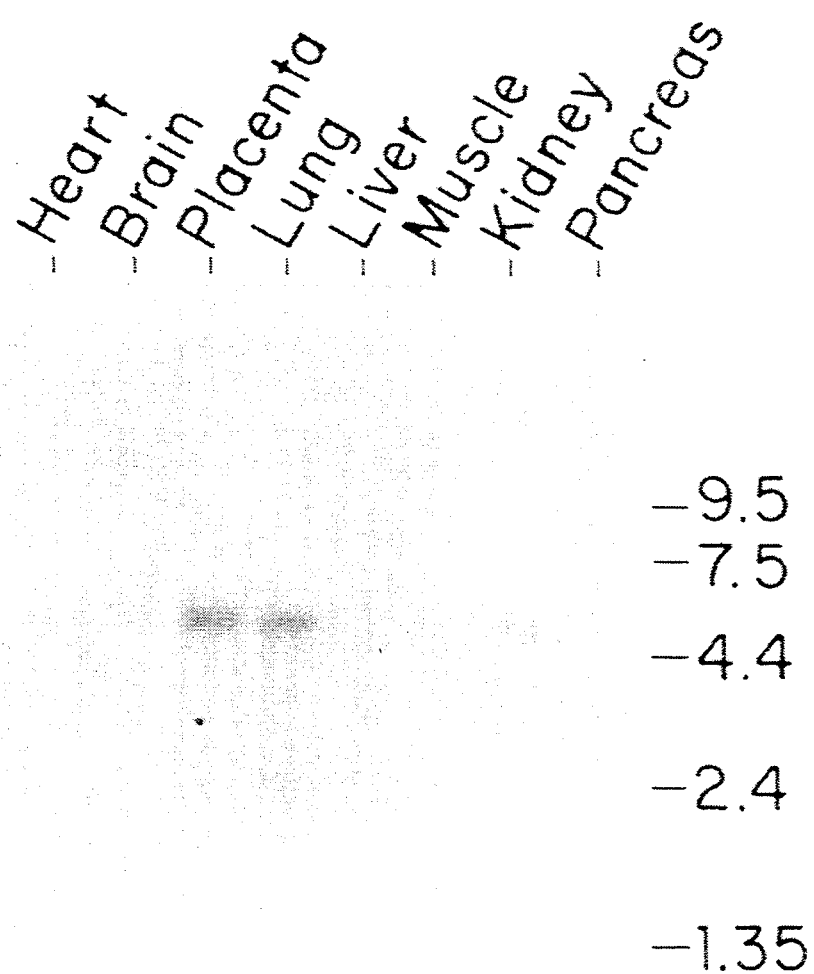
FIG. 4 shows the results of a study of expression of ork mRNA in human tissues, as described in example 3 below. Two micrograms of poly(A)-containing RNA from the indicated tissues was hybridized with an $^{32}$P-UTP-labelled RNA probe from the ork cDNA. The positions of size standards are marked.

RNAs from several human tissues were screened for ork transcripts. For ork expression, a filter containing 2 μg of poly(A)+RNA from various human tissues (Clontech, San Diego, Calif.) was hybridized with an antisense RNA probe containing nucleotides 2240-3005 (outside of the kinase domain). As shown in FIG. 4, a 4.5 kb mRNA was found at highest levels in placenta and lung, with lower levels detected in kidney and heart. Each of these tissues is highly vascularized, suggesting that ork may be expressed in endothelial cells. Consistent with this, umbilical cord vein endothelial cells (HUVECs) also expressed ork message. In addition to the tissues listed in FIG. 4, RNAs isolated from hematopoietic cell lines and tissues were surveyed, but ork mRNA was not detected.

EXAMPLE 4

Monoclonal Antibodies Directed Against ork

This example illustrates the preparation of monoclonal antibodies to ork or immunogenic fragments thereof. Purified ork can be used to generate anti-ork monoclonal antibodies using conventional techniques, for example, those techniques described in U.S. Pat. No. 4,411,993.

In one embodiment of the invention, the peptide used to generate rabbit polyclonal antiserum in example 2 is used to produce a monoclonal antibody. The peptide comprises the carboxy-terminal 21 amino acids of the ork protein (i.e., the last 21 amino acids of the cytoplasmic domain in the (SEQ ID No: 1) sequence) conjugated to ovalbumin. Briefly, mice are immunized with the immunogenic peptide emulsified in complete Freund's adjuvant, and injected in amounts ranging from 10-100 μg subcutaneously or intraperitoneally. Ten to twelve days later, the immunized animals are boosted with additional immunogenic peptide emulsified in incomplete Freund's adjuvant. Mice are periodically boosted thereafter on a weekly to bi-weekly immunization schedule. Serum samples are periodically taken by retro-orbital bleeding or tail-tip excision for testing by dot blot assay or ELISA (Enzyme-Linked. Immunosorbent Assay), for anti-ork antibodies.

Following detection of an appropriate antibody liter, positive animals are provided one last intravenous injection of the immunogen in saline. Three to four days later, the animals are sacrificed, spleen cells harvested, and spleen cells are fused to a murine myeloma cell line (e.g., NS1 or Ag 8.653). Fusions generate hybridoma cells, which are plated in multiple microtiter plates in a. HAT (hypoxanthine, aminopterin and thymidine) selective medium to inhibit proliferation of non-fused cells, myeloma hybrids, and spleen cell hybrids.

The hybridoma cells are screened by ELISA for reactivity against purified ork peptide by adaptations of the techniques disclosed in Engvall et al., *Immunocherm.* 8:871, 1971 and in U.S. Pat. No. 4,703,004. Positive hybridoma cells can be injected intraperitoneally into syngeneic BALB/c mice to produce ascites containing high concentrations of anti-ork monoclonal antibodies. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to protein A or protein G can also be used, as can affinity chromatography based upon binding to ork.

EXAMPLE 5

Cloning of Murine ork cDNA

Murine ork cDNA was isolated by cross-species hybridization using human ork cDNA as a probe. A murine cDNA library was prepared from 12½ day old mouse embryos. The library was screened by conventional techniques using the radiolabeled 2.3 Kb human ork cDNA described in example 1 as a probe.

The DNA sequence of the cDNA insert of a hybridizing clone was determined, and the amino acid sequence encoded thereby is presented in FIG. 6. The murine ork sequence (designated "m"; in the top rows) is aligned with the corresponding portion of human ork ("h") in (SEQ ID No: 3) FIG. 6. Identical amino acids are indicated with a line; conservative or similar amino acid changes are indicated with two dots or one dot, respectively. The percent similarity of these murine and human ork amino acid sequences is 99.2% and the percent identity is 97.5%, as determined by the GAP computer program.

The murine ork sequence corresponds to amino acids 886–1124 of human ork, a region falling within the cytoplasmic domain and extending to the C-terminus of the human ork protein. The murine cDNA may be used as a probe to screen the same or a different murine cDNA library to identify a full length murine ork clone. Alternatively, given the similarity of the human and murine sequences, murine libraries may be screened using a probe derived from the extracellular region of human ork.

What is claimed is:

1. An isolated and purified DNA sequence encoding a human ork polypeptide comprising amino acids 19–1124 of SEQ ID No: 2.

2. An isolated and purified DNA sequence according to claim 1, wherein said DNA sequence comprises nucleotides 203–3523 of SEQ ID NO: 1.

3. An isolated and purified DNA sequence encoding a human ork polypeptide comprising amino acids 19–745 of SEQ ID No: 2.

4. An isolated and purified DNA sequence according to claim 3, wherein said DNA sequence comprises nucleotides 203–3523 of SEQ ID NO: 1.

5. An expression vector comprising a DNA sequence according to claim 1.

6. An expression vector comprising a DNA sequence according to claim 2.

7. An expression vector comprising a DNA sequence according to claim 3.

8. A host cell transformed or transfected with an expression vector according to claim 5.

9. A host cell transformed or transfected with an expression vector according to claim 6.

10. A host cell transformed or transfected with an expression vector according to claim 7.

* * * * *

UNITED STATES PATENT AND TRADEMARK OFFICE
CERTIFICATE OF CORRECTION

PATENT NO.   : 5,447,860
DATED        : September 5, 1995
INVENTOR(S)  : Steven F. Ziegler It is certified that error appears in the above-identified patent and that said Letters Patent is hereby corrected as shown below:

Claim 4,
Line 3, "3523" should read -- 2383 --.

Column 2,
Line 51, "are" should read -- one --.

Column 4,
Line 27, delete "Several".
Line 29, "SEQ ID NO:2 feaures" should read -- SEQ ID NO:2. Several features --.

Column 5,
Line 29, "pans" should read -- parts --.

Column 6,
Line 45, "16" should read -- 1 --.

Signed and Sealed this

Sixteenth Day of April, 2002

Attest:

JAMES E. ROGAN
*Attesting Officer*  *Director of the United States Patent and Trademark Office*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 4138 base pairs
( B ) TYPE: nucleic acid
( C ) STRANDEDNESS: single
( D ) TOPOLOGY: linear ( i i ) MOLECULE TYPE: cDNA to mRNA ( i x ) FEATURE:
( A ) NAME/KEY: CDS
( B ) LOCATION: 149..3523

( x i ) SEQUENCE DESCRIPTION: SEQ ID NO:1:

```
CTTCTGTGCT GTTCCTTCTT GCCTCTAACT TGTAAACAAG ACGTACTAGG ACGATGCTAA      60

TGGAAAGTCA CAAACCGCTG GGTTTTTGAA AGGATCCTTG GGACCTCATG CACATTTGTG     120

GAAACTGGAT GGAGAGATTT GGGGAAGC ATG GAC TCT TTA GCC AGC TTA GTT       172
                                Met Asp Ser Leu Ala Ser Leu Val
                                  1               5

CTC TGT GGA GTC AGC TTG CTC CTT TCT GGA ACT GTG GAA GGT GCC ATG       220
Leu Cys Gly Val Ser Leu Leu Leu Ser Gly Thr Val Glu Gly Ala Met
         10                  15                  20

GAC TTG ATC TTG ATC AAT TCC CTA CCT CTT GTA TCT GAT GCT GAA ACA       268
Asp Leu Ile Leu Ile Asn Ser Leu Pro Leu Val Ser Asp Ala Glu Thr
 25                  30                  35                  40

TCT CTC ACC TGC ATT GCC TCT GGG TGG CGC CCC CAT GAG CCC ATC ACC       316
Ser Leu Thr Cys Ile Ala Ser Gly Trp Arg Pro His Glu Pro Ile Thr
                 45                  50                  55

ATA GGA AGG GAC TTT GAA GCC TTA ATG AAC CAG CAC CAG GAT CCG CTG       364
Ile Gly Arg Asp Phe Glu Ala Leu Met Asn Gln His Gln Asp Pro Leu
             60                  65                  70

GAA GTT ACT CAA GAT GTG ACC AGA GAA TGG GCT AAA AAA GTT GTT TGG       412
Glu Val Thr Gln Asp Val Thr Arg Glu Trp Ala Lys Lys Val Val Trp
         75                  80                  85

AAG AGA GAA AAG GCT AGT AAG ATC AAT GGT GCT TAT TTC TGT GAA GGG       460
Lys Arg Glu Lys Ala Ser Lys Ile Asn Gly Ala Tyr Phe Cys Glu Gly
     90                  95                 100

CGA GTT CGA GGA GAG GCA ATC AGG ATA CGA ACC ATG AAG ATG CGT CAA       508
Arg Val Arg Gly Glu Ala Ile Arg Ile Arg Thr Met Lys Met Arg Gln
105                 110                 115                 120

CAA GCT TCC TTC CTA CCA GCT ACT TTA ACT ATG ACT GTG GAC AAG GGA       556
Gln Ala Ser Phe Leu Pro Ala Thr Leu Thr Met Thr Val Asp Lys Gly
                125                 130                 135

GAT AAC GTG AAC ATA TCT TTC AAA AAG GTA TTG ATT AAA GAA GAA GAT       604
Asp Asn Val Asn Ile Ser Phe Lys Lys Val Leu Ile Lys Glu Glu Asp
            140                 145                 150

GCA GTG ATT TAC AAA AAT GGT TCC TTC ATC CAT TCA GTG CCC CGG CAT       652
Ala Val Ile Tyr Lys Asn Gly Ser Phe Ile His Ser Val Pro Arg His
        155                 160                 165

GAA GTA CCT GAT ATT CTA GAA GTA CAC CTG CCT CAT GCT CAG CCC CAG       700
```

-continued

|     |     |     |     |     |     |     |     |     |     |     |     |     |     |     |      |
|-----|-----|-----|-----|-----|-----|-----|-----|-----|-----|-----|-----|-----|-----|-----|------|
| Glu | Val | Pro | Asp | Ile | Leu | Glu | Val | His | Leu | Pro | His | Ala | Gln | Pro | Gln  |
|     | 170 |     |     |     | 175 |     |     |     |     | 180 |     |     |     |     |      |

| GAT | GCT | GGA | GTG | TAC | TCG | GCC | AGG | TAT | ATA | GGA | GGA | AAC | CTC | TTC | ACC | 748  |
|-----|-----|-----|-----|-----|-----|-----|-----|-----|-----|-----|-----|-----|-----|-----|-----|------|
| Asp | Ala | Gly | Val | Tyr | Ser | Ala | Arg | Tyr | Ile | Gly | Gly | Asn | Leu | Phe | Thr |      |
| 185 |     |     |     |     | 190 |     |     |     |     | 195 |     |     |     |     | 200 |      |

| TCG | GCC | TTC | ACC | AGG | CTG | ATA | GTC | CGG | AGA | TGT | GAA | GCC | CAG | AAG | TGG | 796  |
|-----|-----|-----|-----|-----|-----|-----|-----|-----|-----|-----|-----|-----|-----|-----|-----|------|
| Ser | Ala | Phe | Thr | Arg | Leu | Ile | Val | Arg | Arg | Cys | Glu | Ala | Gln | Lys | Trp |      |
|     |     |     |     | 205 |     |     |     |     | 210 |     |     |     |     | 215 |     |      |

| GGA | CCT | GAA | TGC | AAC | CAT | CTC | TGT | ACT | GCT | TGT | ATG | AAC | AAT | GGT | GTC | 844  |
|-----|-----|-----|-----|-----|-----|-----|-----|-----|-----|-----|-----|-----|-----|-----|-----|------|
| Gly | Pro | Glu | Cys | Asn | His | Leu | Cys | Thr | Ala | Cys | Met | Asn | Asn | Gly | Val |      |
|     |     |     | 220 |     |     |     |     | 225 |     |     |     |     | 230 |     |     |      |

| TGC | CAT | GAA | GAT | ACT | GGA | GAA | TGC | ATT | TGC | CCT | CCT | GGG | TTT | ATG | GGA | 892  |
|-----|-----|-----|-----|-----|-----|-----|-----|-----|-----|-----|-----|-----|-----|-----|-----|------|
| Cys | His | Glu | Asp | Thr | Gly | Glu | Cys | Ile | Cys | Pro | Pro | Gly | Phe | Met | Gly |      |
|     |     | 235 |     |     |     |     | 240 |     |     |     |     | 245 |     |     |     |      |

| AGG | ACG | TGT | GAG | AAG | GCT | TGT | GAA | CTG | CAC | ACG | TTT | GGC | AGA | ACT | TGT | 940  |
|-----|-----|-----|-----|-----|-----|-----|-----|-----|-----|-----|-----|-----|-----|-----|-----|------|
| Arg | Thr | Cys | Glu | Lys | Ala | Cys | Glu | Leu | His | Thr | Phe | Gly | Arg | Thr | Cys |      |
|     | 250 |     |     |     |     | 255 |     |     |     |     | 260 |     |     |     |     |      |

| AAA | GAA | AGG | TGC | AGT | GGA | CAA | GAG | GGA | TGC | AAG | TCT | TAT | GTG | TTC | TGT | 988  |
|-----|-----|-----|-----|-----|-----|-----|-----|-----|-----|-----|-----|-----|-----|-----|-----|------|
| Lys | Glu | Arg | Cys | Ser | Gly | Gln | Glu | Gly | Cys | Lys | Ser | Tyr | Val | Phe | Cys |      |
| 265 |     |     |     |     | 270 |     |     |     |     | 275 |     |     |     |     | 280 |      |

| CTC | CCT | GAC | CCC | TAT | GGG | TGT | TCC | TGT | GCC | ACA | GGC | TGG | AAG | GGT | CTG | 1036 |
|-----|-----|-----|-----|-----|-----|-----|-----|-----|-----|-----|-----|-----|-----|-----|-----|------|
| Leu | Pro | Asp | Pro | Tyr | Gly | Cys | Ser | Cys | Ala | Thr | Gly | Trp | Lys | Gly | Leu |      |
|     |     |     |     | 285 |     |     |     |     | 290 |     |     |     |     | 295 |     |      |

| CAG | TGC | AAT | GAA | GCA | TGC | CAC | CCT | GGT | TTT | TAC | GGG | CCA | GAT | TGT | AAG | 1084 |
|-----|-----|-----|-----|-----|-----|-----|-----|-----|-----|-----|-----|-----|-----|-----|-----|------|
| Gln | Cys | Asn | Glu | Ala | Cys | His | Pro | Gly | Phe | Tyr | Gly | Pro | Asp | Cys | Lys |      |
|     |     | 300 |     |     |     |     | 305 |     |     |     |     | 310 |     |     |     |      |

| CTT | AGG | TGC | AGC | TGC | AAC | AAT | GGG | GAG | ATG | TGT | GAT | CGC | TTC | CAA | GGA | 1132 |
|-----|-----|-----|-----|-----|-----|-----|-----|-----|-----|-----|-----|-----|-----|-----|-----|------|
| Leu | Arg | Cys | Ser | Cys | Asn | Asn | Gly | Glu | Met | Cys | Asp | Arg | Phe | Gln | Gly |      |
|     |     | 315 |     |     |     |     | 320 |     |     |     |     | 325 |     |     |     |      |

| TGT | CTC | TGC | TCT | CCA | GGA | TGG | CAG | GGG | CTC | CAG | TGT | GAG | AGA | GAA | GGC | 1180 |
|-----|-----|-----|-----|-----|-----|-----|-----|-----|-----|-----|-----|-----|-----|-----|-----|------|
| Cys | Leu | Cys | Ser | Pro | Gly | Trp | Gln | Gly | Leu | Gln | Cys | Glu | Arg | Glu | Gly |      |
| 330 |     |     |     |     | 335 |     |     |     |     | 340 |     |     |     |     |     |      |

| ATA | CCG | AGG | ATG | ACC | CCA | AAG | ATA | GTG | GAT | TTG | CCA | GAT | CAT | ATA | GAA | 1228 |
|-----|-----|-----|-----|-----|-----|-----|-----|-----|-----|-----|-----|-----|-----|-----|-----|------|
| Ile | Pro | Arg | Met | Thr | Pro | Lys | Ile | Val | Asp | Leu | Pro | Asp | His | Ile | Glu |      |
| 345 |     |     |     |     | 350 |     |     |     |     | 355 |     |     |     |     | 360 |      |

| GTA | AAC | AGT | GGT | AAA | TTT | AAT | CCC | ATT | TGC | AAA | GCT | TCT | GGC | TGG | CCG | 1276 |
|-----|-----|-----|-----|-----|-----|-----|-----|-----|-----|-----|-----|-----|-----|-----|-----|------|
| Val | Asn | Ser | Gly | Lys | Phe | Asn | Pro | Ile | Cys | Lys | Ala | Ser | Gly | Trp | Pro |      |
|     |     |     |     | 365 |     |     |     |     | 370 |     |     |     |     | 375 |     |      |

| CTA | CCT | ACT | AAT | GAA | GAA | ATG | ACC | CTG | GTG | AAG | CCG | GAT | GGG | ACA | GTG | 1324 |
|-----|-----|-----|-----|-----|-----|-----|-----|-----|-----|-----|-----|-----|-----|-----|-----|------|
| Leu | Pro | Thr | Asn | Glu | Glu | Met | Thr | Leu | Val | Lys | Pro | Asp | Gly | Thr | Val |      |
|     |     |     | 380 |     |     |     |     | 385 |     |     |     |     | 390 |     |     |      |

| CTC | CAT | CCA | AAA | GAC | TTT | AAC | CAT | ACG | GAT | CAT | TTC | TCA | GTA | GCC | ATA | 1372 |
|-----|-----|-----|-----|-----|-----|-----|-----|-----|-----|-----|-----|-----|-----|-----|-----|------|
| Leu | His | Pro | Lys | Asp | Phe | Asn | His | Thr | Asp | His | Phe | Ser | Val | Ala | Ile |      |
|     |     | 395 |     |     |     |     | 400 |     |     |     |     | 405 |     |     |     |      |

| TTC | ACC | ATC | CAC | CGG | ATC | CTC | CCC | CCT | GAC | TCA | GGA | GTT | TGG | GTC | TGC | 1420 |
|-----|-----|-----|-----|-----|-----|-----|-----|-----|-----|-----|-----|-----|-----|-----|-----|------|
| Phe | Thr | Ile | His | Arg | Ile | Leu | Pro | Pro | Asp | Ser | Gly | Val | Trp | Val | Cys |      |
| 410 |     |     |     |     | 415 |     |     |     |     | 420 |     |     |     |     |     |      |

| AGT | GTG | AAC | ACA | GTG | GCT | GGG | ATG | GTG | GAA | AAG | CCC | TTC | AAC | ATT | TCT | 1468 |
|-----|-----|-----|-----|-----|-----|-----|-----|-----|-----|-----|-----|-----|-----|-----|-----|------|
| Ser | Val | Asn | Thr | Val | Ala | Gly | Met | Val | Glu | Lys | Pro | Phe | Asn | Ile | Ser |      |
| 425 |     |     |     |     | 430 |     |     |     |     | 435 |     |     |     |     | 440 |      |

| GTT | AAA | GTT | CTT | CCA | AAG | CCC | CTG | AAT | GCC | CCA | AAC | GTG | ATT | GAC | ACT | 1516 |
|-----|-----|-----|-----|-----|-----|-----|-----|-----|-----|-----|-----|-----|-----|-----|-----|------|
| Val | Lys | Val | Leu | Pro | Lys | Pro | Leu | Asn | Ala | Pro | Asn | Val | Ile | Asp | Thr |      |
|     |     |     |     | 445 |     |     |     |     | 450 |     |     |     |     | 455 |     |      |

| GGA | CAT | AAC | TTT | GCT | GTC | ATC | AAC | ATC | AGC | TCT | GAG | CCT | TAC | TTT | GGG | 1564 |
|-----|-----|-----|-----|-----|-----|-----|-----|-----|-----|-----|-----|-----|-----|-----|-----|------|
| Gly | His | Asn | Phe | Ala | Val | Ile | Asn | Ile | Ser | Ser | Glu | Pro | Tyr | Phe | Gly |      |
|     |     |     | 460 |     |     |     |     | 465 |     |     |     |     | 470 |     |     |      |

| GAT | GGA | CCA | ATC | AAA | TCC | AAG | AAG | CTT | CTA | TAC | AAA | CCC | GTT | AAT | CAC | 1612 |
|-----|-----|-----|-----|-----|-----|-----|-----|-----|-----|-----|-----|-----|-----|-----|-----|------|
| Asp | Gly | Pro | Ile | Lys | Ser | Lys | Lys | Leu | Leu | Tyr | Lys | Pro | Val | Asn | His |      |
|     |     | 475 |     |     |     |     | 480 |     |     |     |     | 485 |     |     |     |      |

| TAT | GAG | GCT | TGG | CAA | CAT | ATT | CAA | GTG | ACA | AAT | GAG | ATT | GTT | ACA | CTC | 1660 |
|-----|-----|-----|-----|-----|-----|-----|-----|-----|-----|-----|-----|-----|-----|-----|-----|------|
| Tyr | Glu | Ala | Trp | Gln | His | Ile | Gln | Val | Thr | Asn | Glu | Ile | Val | Thr | Leu |      |
|     | 490 |     |     |     |     | 495 |     |     |     |     | 500 |     |     |     |     |      |

| | | | | | | | | | | | | | | | | |
|---|---|---|---|---|---|---|---|---|---|---|---|---|---|---|---|---|
| AAC | TAT | TTG | GAA | CCT | CGG | ACA | GAA | TAT | GAA | CTC | TGT | GTG | CAA | CTG | GTC | 1708 |
| Asn | Tyr | Leu | Glu | Pro | Arg | Thr | Glu | Tyr | Glu | Leu | Cys | Val | Gln | Leu | Val | |
| 505 | | | | 510 | | | | | 515 | | | | | | 520 | |
| CGT | CGT | GGA | GAG | GGT | GGG | GAA | GGG | CAT | CCT | GGA | CCT | GTG | AGA | CGC | TTC | 1756 |
| Arg | Arg | Gly | Glu | Gly | Gly | Glu | Gly | His | Pro | Gly | Pro | Val | Arg | Arg | Phe | |
| | | | | 525 | | | | | 530 | | | | | 535 | | |
| ACA | ACA | GCT | TCT | ATC | GGA | CTC | CCT | CCT | CCA | AGA | GGT | CTA | AAT | CTC | CTG | 1804 |
| Thr | Thr | Ala | Ser | Ile | Gly | Leu | Pro | Pro | Pro | Arg | Gly | Leu | Asn | Leu | Leu | |
| | | | 540 | | | | | 545 | | | | | 550 | | | |
| CCT | AAA | AGT | CAG | ACC | ACT | CTA | AAT | TTG | ACC | TGG | CAA | CCA | ATA | TTT | CCA | 1852 |
| Pro | Lys | Ser | Gln | Thr | Thr | Leu | Asn | Leu | Thr | Trp | Gln | Pro | Ile | Phe | Pro | |
| | | 555 | | | | | 560 | | | | | 565 | | | | |
| AGC | TCG | GAA | GAT | GAC | TTT | TAT | GTT | GAA | GTG | GAG | AGA | AGG | TCT | GTG | CAA | 1900 |
| Ser | Ser | Glu | Asp | Asp | Phe | Tyr | Val | Glu | Val | Glu | Arg | Arg | Ser | Val | Gln | |
| | 570 | | | | | 575 | | | | | 580 | | | | | |
| AAA | AGT | GAT | CAG | CAG | AAT | ATT | AAA | GTT | CCA | GGC | AAC | TTG | ACT | TCG | GTG | 1948 |
| Lys | Ser | Asp | Gln | Gln | Asn | Ile | Lys | Val | Pro | Gly | Asn | Leu | Thr | Ser | Val | |
| 585 | | | | | 590 | | | | | 595 | | | | | 600 | |
| CTA | CTT | AAC | AAC | TTA | CAT | CCC | AGG | GAG | CAG | TAC | GTG | GTC | CGA | GCT | AGA | 1996 |
| Leu | Leu | Asn | Asn | Leu | His | Pro | Arg | Glu | Gln | Tyr | Val | Val | Arg | Ala | Arg | |
| | | | | 605 | | | | | 610 | | | | | 615 | | |
| GTC | AAC | ACC | AAG | GCC | CAG | GGG | GAA | TGG | AGT | GAA | GAT | CTC | ACT | GCT | TGG | 2044 |
| Val | Asn | Thr | Lys | Ala | Gln | Gly | Glu | Trp | Ser | Glu | Asp | Leu | Thr | Ala | Trp | |
| | | | 620 | | | | | 625 | | | | | 630 | | | |
| ACC | CTT | AGT | GAC | ATT | CTT | CCT | CCT | CAA | CCA | GAA | AAC | ATC | AAG | ATT | TCC | 2092 |
| Thr | Leu | Ser | Asp | Ile | Leu | Pro | Pro | Gln | Pro | Glu | Asn | Ile | Lys | Ile | Ser | |
| | | 635 | | | | | 640 | | | | | 645 | | | | |
| AAC | ATT | ACA | CAC | TCC | TCG | GCT | GTG | ATT | TCT | TGG | ACA | ATA | TTG | GAT | GGC | 2140 |
| Asn | Ile | Thr | His | Ser | Ser | Ala | Val | Ile | Ser | Trp | Thr | Ile | Leu | Asp | Gly | |
| | 650 | | | | | 655 | | | | | 660 | | | | | |
| TAT | TCT | ATT | TCT | TCT | ATT | ACT | ATC | CGT | TAC | AAG | GTT | CAA | GGC | AAG | AAT | 2188 |
| Tyr | Ser | Ile | Ser | Ser | Ile | Thr | Ile | Arg | Tyr | Lys | Val | Gln | Gly | Lys | Asn | |
| 665 | | | | | 670 | | | | | 675 | | | | | 680 | |
| GAA | GAC | CAG | CAC | GTT | GAT | GTG | AAG | ATA | AAG | AAT | GCC | ACC | ATC | ATT | CAG | 2236 |
| Glu | Asp | Gln | His | Val | Asp | Val | Lys | Ile | Lys | Asn | Ala | Thr | Ile | Ile | Gln | |
| | | | | 685 | | | | | 690 | | | | | 695 | | |
| TAT | CAG | CTC | AAG | GGC | CTA | GAG | CCT | GAA | ACA | GCA | TAC | CAG | GTG | GAC | ATT | 2284 |
| Tyr | Gln | Leu | Lys | Gly | Leu | Glu | Pro | Glu | Thr | Ala | Tyr | Gln | Val | Asp | Ile | |
| | | | 700 | | | | | 705 | | | | | 710 | | | |
| TTT | GCA | GAG | AAC | AAC | ATA | GGG | TCA | AGC | AAC | CCA | GCC | TTT | TCT | CAT | GAA | 2332 |
| Phe | Ala | Glu | Asn | Asn | Ile | Gly | Ser | Ser | Asn | Pro | Ala | Phe | Ser | His | Glu | |
| | | 715 | | | | | 720 | | | | | 725 | | | | |
| CTG | GTG | ACC | CTC | CCA | GAA | TCT | CAA | GCA | CCA | GCG | GAC | CTC | GGA | GGG | GGG | 2380 |
| Leu | Val | Thr | Leu | Pro | Glu | Ser | Gln | Ala | Pro | Ala | Asp | Leu | Gly | Gly | Gly | |
| | | 730 | | | | | 735 | | | | | 740 | | | | |
| AAG | ATG | CTG | CTT | ATA | GCC | ATC | CTT | GGC | TCT | GCT | GGA | ATG | ACC | TGC | CTG | 2428 |
| Lys | Met | Leu | Leu | Ile | Ala | Ile | Leu | Gly | Ser | Ala | Gly | Met | Thr | Cys | Leu | |
| 745 | | | | | 750 | | | | | 755 | | | | | 760 | |
| ACT | GTG | CTG | TTG | GCC | TTT | CTG | ATC | ATA | TTG | CAA | TTG | AAG | AGG | GCA | AAT | 2476 |
| Thr | Val | Leu | Leu | Ala | Phe | Leu | Ile | Ile | Leu | Gln | Leu | Lys | Arg | Ala | Asn | |
| | | | | 765 | | | | | 770 | | | | | 775 | | |
| GTG | CAA | AGG | AGA | ATG | GCC | CAA | GCC | TTC | CAA | AAC | GTG | AGG | GAA | GAA | CCA | 2524 |
| Val | Gln | Arg | Arg | Met | Ala | Gln | Ala | Phe | Gln | Asn | Val | Arg | Glu | Glu | Pro | |
| | | | 780 | | | | | 785 | | | | | 790 | | | |
| GCT | GTG | CAG | TTC | AAC | TCA | GGG | ACT | CTG | GCC | CTA | AAC | AGG | AAG | GTC | AAA | 2572 |
| Ala | Val | Gln | Phe | Asn | Ser | Gly | Thr | Leu | Ala | Leu | Asn | Arg | Lys | Val | Lys | |
| | | 795 | | | | | 800 | | | | | 805 | | | | |
| AAC | AAC | CCA | GAT | CCT | ACA | ATT | TAT | CCA | GTG | CTT | GAC | TGG | AAT | GAC | ATC | 2620 |
| Asn | Asn | Pro | Asp | Pro | Thr | Ile | Tyr | Pro | Val | Leu | Asp | Trp | Asn | Asp | Ile | |
| | | 810 | | | | | 815 | | | | | 820 | | | | |
| AAA | TTT | CAA | GAT | GTG | ATT | GGG | GAG | GGC | AAT | TTT | GGC | CAA | GTT | CTT | AAG | 2668 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Lys | Phe | Gln | Asp | Val | Ile | Gly | Glu | Gly | Asn | Phe | Gly | Gln | Val | Leu | Lys |      |
| 825 |     |     |     | 830 |     |     |     | 835 |     |     |     |     |     |     | 840 |      |
| GCG | CGC | ATC | AAG | AAG | GAT | GGG | TTA | CGG | ATG | GAT | GCT | GCC | ATC | AAA | AGA | 2716 |
| Ala | Arg | Ile | Lys | Lys | Asp | Gly | Leu | Arg | Met | Asp | Ala | Ala | Ile | Lys | Arg |      |
|     |     |     | 845 |     |     |     |     | 850 |     |     |     |     | 855 |     |     |      |
| ATG | AAA | GAA | TAT | GCC | TCC | AAA | GAT | GAT | CAC | AGG | GAC | TTT | GCA | GGA | GAA | 2764 |
| Met | Lys | Glu | Tyr | Ala | Ser | Lys | Asp | Asp | His | Arg | Asp | Phe | Ala | Gly | Glu |      |
|     |     |     | 860 |     |     |     |     | 865 |     |     |     |     | 870 |     |     |      |
| CTG | GAA | GTT | CTT | TGT | AAA | CTT | GGA | CAC | CAT | CCA | AAC | ATC | ATC | AAT | CTC | 2812 |
| Leu | Glu | Val | Leu | Cys | Lys | Leu | Gly | His | His | Pro | Asn | Ile | Ile | Asn | Leu |      |
|     |     | 875 |     |     |     |     | 880 |     |     |     |     | 885 |     |     |     |      |
| TTA | GGA | GCA | TGT | GAA | CAT | CGA | GGC | TAC | TTG | TAC | CTG | GCC | ATT | GAG | TAC | 2860 |
| Leu | Gly | Ala | Cys | Glu | His | Arg | Gly | Tyr | Leu | Tyr | Leu | Ala | Ile | Glu | Tyr |      |
|     | 890 |     |     |     |     | 895 |     |     |     |     | 900 |     |     |     |     |      |
| GCG | CCC | CAT | GGA | AAC | CTT | CTG | GAC | TTC | CTT | CGC | AAG | AGC | CGT | GTG | CTG | 2908 |
| Ala | Pro | His | Gly | Asn | Leu | Leu | Asp | Phe | Leu | Arg | Lys | Ser | Arg | Val | Leu |      |
| 905 |     |     |     | 910 |     |     |     |     | 915 |     |     |     |     | 920 |     |      |
| GAG | ACG | GAC | CCA | GCA | TTT | GCC | ATT | GCC | AAT | AGC | ACC | GCG | TCC | ACA | CTG | 2956 |
| Glu | Thr | Asp | Pro | Ala | Phe | Ala | Ile | Ala | Asn | Ser | Thr | Ala | Ser | Thr | Leu |      |
|     |     |     |     | 925 |     |     |     | 930 |     |     |     |     | 935 |     |     |      |
| TCC | TCC | CAG | CAG | CTC | CTT | CAC | TTC | GCT | GCC | GAC | GTG | GCC | CGG | GGC | ATG | 3004 |
| Ser | Ser | Gln | Gln | Leu | Leu | His | Phe | Ala | Ala | Asp | Val | Ala | Arg | Gly | Met |      |
|     |     |     | 940 |     |     |     |     | 945 |     |     |     |     | 950 |     |     |      |
| GAC | TAC | TTG | AGC | CAA | AAA | CAG | TTT | ATC | CAC | AGG | GAT | CTG | GCT | GCC | AGA | 3052 |
| Asp | Tyr | Leu | Ser | Gln | Lys | Gln | Phe | Ile | His | Arg | Asp | Leu | Ala | Ala | Arg |      |
|     |     | 955 |     |     |     |     | 960 |     |     |     |     | 965 |     |     |     |      |
| AAC | ATT | TTA | GTT | GGT | GAA | AAC | TAT | GTG | GCA | AAA | ATA | GCA | GAT | TTT | GGA | 3100 |
| Asn | Ile | Leu | Val | Gly | Glu | Asn | Tyr | Val | Ala | Lys | Ile | Ala | Asp | Phe | Gly |      |
|     | 970 |     |     |     |     | 975 |     |     |     |     | 980 |     |     |     |     |      |
| TTG | TCC | CGA | GGT | CAA | GAG | GTG | TAC | GTG | AAA | AAG | ACA | ATG | GGA | AGG | CTC | 3148 |
| Leu | Ser | Arg | Gly | Gln | Glu | Val | Tyr | Val | Lys | Lys | Thr | Met | Gly | Arg | Leu |      |
| 985 |     |     |     |     | 990 |     |     |     |     | 995 |     |     |     |     | 1000 |      |
| CCA | GTG | CGC | TGG | ATG | GCC | ATC | GAG | TCA | CTG | AAT | TAC | AGT | GTG | TAC | ACA | 3196 |
| Pro | Val | Arg | Trp | Met | Ala | Ile | Glu | Ser | Leu | Asn | Tyr | Ser | Val | Tyr | Thr |      |
|     |     |     |     | 1005|     |     |     |     | 1010|     |     |     |     | 1015|     |      |
| ACC | AAC | AGT | GAT | GTA | TGG | TCC | TAT | GGT | GTG | TTA | CTA | TGG | GAG | ATT | GTT | 3244 |
| Thr | Asn | Ser | Asp | Val | Trp | Ser | Tyr | Gly | Val | Leu | Leu | Trp | Glu | Ile | Val |      |
|     |     |     | 1020|     |     |     |     | 1025|     |     |     |     | 1030|     |     |      |
| AGC | TTA | GGA | GGC | ACA | CCC | TAC | TGC | GGG | ATG | ACT | TGT | GCA | GAA | CTC | TAC | 3292 |
| Ser | Leu | Gly | Gly | Thr | Pro | Tyr | Cys | Gly | Met | Thr | Cys | Ala | Glu | Leu | Tyr |      |
|     |     |     | 1035|     |     |     |     | 1040|     |     |     |     | 1045|     |     |      |
| GAG | AAG | CTG | CCC | CAG | GGC | TAC | AGA | CTG | GAG | AAG | CCC | CTG | AAC | TGT | GAT | 3340 |
| Glu | Lys | Leu | Pro | Gln | Gly | Tyr | Arg | Leu | Glu | Lys | Pro | Leu | Asn | Cys | Asp |      |
|     |     |     | 1050|     |     |     |     | 1055|     |     |     |     | 1060|     |     |      |
| GAT | GAG | GTG | TAT | GAT | CTA | ATG | AGA | CAA | TGC | TGG | CGG | GAG | AAG | CCT | TAT | 3388 |
| Asp | Glu | Val | Tyr | Asp | Leu | Met | Arg | Gln | Cys | Trp | Arg | Glu | Lys | Pro | Tyr |      |
| 1065|     |     |     |     | 1070|     |     |     |     | 1075|     |     |     |     | 1080|      |
| GAG | AGG | CCA | TCA | TTT | GCC | CAG | ATA | TTG | GTG | TCC | TTA | AAC | AGA | ATG | TTA | 3436 |
| Glu | Arg | Pro | Ser | Phe | Ala | Gln | Ile | Leu | Val | Ser | Leu | Asn | Arg | Met | Leu |      |
|     |     |     |     | 1085|     |     |     |     | 1090|     |     |     |     | 1095|     |      |
| GAG | GAG | CGA | AAG | ACC | TAC | GTG | AAT | ACC | ACG | CTT | TAT | GAG | AAG | TTT | ACT | 3484 |
| Glu | Glu | Arg | Lys | Thr | Tyr | Val | Asn | Thr | Thr | Leu | Tyr | Glu | Lys | Phe | Thr |      |
|     |     |     |     | 1100|     |     |     |     | 1105|     |     |     |     | 1110|     |      |
| TAT | GCA | GGA | ATT | GAC | TGT | TCT | GCT | GAA | GAA | GCG | GCC | TAGGACAGAA |     |     |     | 3530 |
| Tyr | Ala | Gly | Ile | Asp | Cys | Ser | Ala | Glu | Glu | Ala | Ala |     |     |     |     |      |
|     |     |     |     | 1115|     |     |     | 1120|     |     | 112 |     |     |     |     |      |

```
CATCTGTATA  CCCTCTGTTT  CCCTTTCACT  GGCATGGGAG  ACCCTTGACA  ACTGCTGAGA   3590

AAACATGCCT  CTGCCAAAGG  ATGTGATATA  TAAGTGTACA  TATGTGCTGG  AATTCTAACA   3650

AGTCATAGGT  TAATATTTAA  GACACTGAAA  AATCTAAGTG  ATATAAATCA  GATTCTTCTC   3710

TCTCATTTTA  TCCCTCACCT  GTAGCATGCC  AGTCCCGTTT  CATTTAGTCA  TGTGACCACT   3770
```

```
CTGTCTTGTG TTTCCACAGC CTGCAAGTTC AGTCCAGGAT GCTAACATCT AAAAATAGAC   3830

TTAAATCTCA TTGCTTACAA GCCTAAGAAT CTTTAGAGAA GTATACATAA GTTTAGGATA   3890

AAATAATGGG ATTTTCTTTT CTTTTCTCTG GTAATATTGA CTTGTATATT TTAAGAAATA   3950

ACAGAAAGCC TGGGTGACAT TTGGGAGACA TGTGACATTT ATATATTGAA TTAATATCCC   4010

TACATGTATT GCACATTGTA AAAGTTTTA GTTTTGATGA GTTGTGAGTT TACCTTGTAT    4070

ACTGTAGGCA CACTTTGCAC TGATATATCA TGAGTGAATA AATGTCTTGC CTACTCAAAA   4130

AAAAAAAA                                                            4138
```

( 2 ) INFORMATION FOR SEQ ID NO:2:

( i ) SEQUENCE CHARACTERISTICS:
        ( A ) LENGTH: 1124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Ser Leu Ala Ser Leu Val Leu Cys Gly Val Ser Leu Leu Leu
 1               5                  10                  15

Ser Gly Thr Val Glu Gly Ala Met Asp Leu Ile Leu Ile Asn Ser Leu
             20                  25                  30

Pro Leu Val Ser Asp Ala Glu Thr Ser Leu Thr Cys Ile Ala Ser Gly
         35                  40                  45

Trp Arg Pro His Glu Pro Ile Thr Ile Gly Arg Asp Phe Glu Ala Leu
     50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
```

-continued

|     | 290 |     |     |     | 295 |     |     |     | 300 |     |     |     |     |
|---|---|---|---|---|---|---|---|---|---|---|---|---|---|
| Gly | Phe | Tyr | Gly | Pro | Asp | Cys | Lys | Leu | Arg | Cys | Ser | Cys | Asn | Asn | Gly |
| 305 |  |  |  |  | 310 |  |  |  | 315 |  |  |  |  |  | 320 |
| Glu | Met | Cys | Asp | Arg | Phe | Gln | Gly | Cys | Leu | Cys | Ser | Pro | Gly | Trp | Gln |
|  |  |  |  | 325 |  |  |  |  | 330 |  |  |  |  | 335 |  |
| Gly | Leu | Gln | Cys | Glu | Arg | Glu | Gly | Ile | Pro | Arg | Met | Thr | Pro | Lys | Ile |
|  |  |  | 340 |  |  |  |  | 345 |  |  |  |  | 350 |  |  |
| Val | Asp | Leu | Pro | Asp | His | Ile | Glu | Val | Asn | Ser | Gly | Lys | Phe | Asn | Pro |
|  |  | 355 |  |  |  |  | 360 |  |  |  |  | 365 |  |  |  |
| Ile | Cys | Lys | Ala | Ser | Gly | Trp | Pro | Leu | Pro | Thr | Asn | Glu | Glu | Met | Thr |
|  | 370 |  |  |  |  | 375 |  |  |  |  | 380 |  |  |  |  |
| Leu | Val | Lys | Pro | Asp | Gly | Thr | Val | Leu | His | Pro | Lys | Asp | Phe | Asn | His |
| 385 |  |  |  |  | 390 |  |  |  |  | 395 |  |  |  |  | 400 |
| Thr | Asp | His | Phe | Ser | Val | Ala | Ile | Phe | Thr | Ile | His | Arg | Ile | Leu | Pro |
|  |  |  |  | 405 |  |  |  |  | 410 |  |  |  |  | 415 |  |
| Pro | Asp | Ser | Gly | Val | Trp | Val | Cys | Ser | Val | Asn | Thr | Val | Ala | Gly | Met |
|  |  |  | 420 |  |  |  |  | 425 |  |  |  |  | 430 |  |  |
| Val | Glu | Lys | Pro | Phe | Asn | Ile | Ser | Val | Lys | Val | Leu | Pro | Lys | Pro | Leu |
|  |  | 435 |  |  |  |  | 440 |  |  |  |  | 445 |  |  |  |
| Asn | Ala | Pro | Asn | Val | Ile | Asp | Thr | Gly | His | Asn | Phe | Ala | Val | Ile | Asn |
| 450 |  |  |  |  | 455 |  |  |  |  | 460 |  |  |  |  |  |
| Ile | Ser | Ser | Glu | Pro | Tyr | Phe | Gly | Asp | Gly | Pro | Ile | Lys | Ser | Lys | Lys |
| 465 |  |  |  |  | 470 |  |  |  |  | 475 |  |  |  |  | 480 |
| Leu | Leu | Tyr | Lys | Pro | Val | Asn | His | Tyr | Glu | Ala | Trp | Gln | His | Ile | Gln |
|  |  |  |  | 485 |  |  |  |  | 490 |  |  |  |  | 495 |  |
| Val | Thr | Asn | Glu | Ile | Val | Thr | Leu | Asn | Tyr | Leu | Glu | Pro | Arg | Thr | Glu |
|  |  |  | 500 |  |  |  |  | 505 |  |  |  |  | 510 |  |  |
| Tyr | Glu | Leu | Cys | Val | Gln | Leu | Val | Arg | Arg | Gly | Glu | Gly | Gly | Glu | Gly |
|  |  | 515 |  |  |  |  | 520 |  |  |  |  | 525 |  |  |  |
| His | Pro | Gly | Pro | Val | Arg | Arg | Phe | Thr | Thr | Ala | Ser | Ile | Gly | Leu | Pro |
|  | 530 |  |  |  |  | 535 |  |  |  |  | 540 |  |  |  |  |
| Pro | Pro | Arg | Gly | Leu | Asn | Leu | Leu | Pro | Lys | Ser | Gln | Thr | Thr | Leu | Asn |
| 545 |  |  |  |  | 550 |  |  |  |  | 555 |  |  |  |  | 560 |
| Leu | Thr | Trp | Gln | Pro | Ile | Phe | Pro | Ser | Ser | Glu | Asp | Asp | Phe | Tyr | Val |
|  |  |  |  | 565 |  |  |  |  | 570 |  |  |  |  | 575 |  |
| Glu | Val | Glu | Arg | Arg | Ser | Val | Gln | Lys | Ser | Asp | Gln | Gln | Asn | Ile | Lys |
|  |  |  | 580 |  |  |  |  | 585 |  |  |  |  | 590 |  |  |
| Val | Pro | Gly | Asn | Leu | Thr | Ser | Val | Leu | Leu | Asn | Asn | Leu | His | Pro | Arg |
|  |  | 595 |  |  |  |  | 600 |  |  |  |  | 605 |  |  |  |
| Glu | Gln | Tyr | Val | Val | Arg | Ala | Arg | Val | Asn | Thr | Lys | Ala | Gln | Gly | Glu |
| 610 |  |  |  |  | 615 |  |  |  |  | 620 |  |  |  |  |  |
| Trp | Ser | Glu | Asp | Leu | Thr | Ala | Trp | Thr | Leu | Ser | Asp | Ile | Leu | Pro | Pro |
| 625 |  |  |  |  | 630 |  |  |  |  | 635 |  |  |  |  | 640 |
| Gln | Pro | Glu | Asn | Ile | Lys | Ile | Ser | Asn | Ile | Thr | His | Ser | Ser | Ala | Val |
|  |  |  |  | 645 |  |  |  |  | 650 |  |  |  |  | 655 |  |
| Ile | Ser | Trp | Thr | Ile | Leu | Asp | Gly | Tyr | Ser | Ile | Ser | Ser | Ile | Thr | Ile |
|  |  |  | 660 |  |  |  |  | 665 |  |  |  |  | 670 |  |  |
| Arg | Tyr | Lys | Val | Gln | Gly | Lys | Asn | Glu | Asp | Gln | His | Val | Asp | Val | Lys |
|  |  | 675 |  |  |  |  | 680 |  |  |  |  | 685 |  |  |  |
| Ile | Lys | Asn | Ala | Thr | Ile | Ile | Gln | Tyr | Gln | Leu | Lys | Gly | Leu | Glu | Pro |
|  | 690 |  |  |  |  | 695 |  |  |  |  | 700 |  |  |  |  |
| Glu | Thr | Ala | Tyr | Gln | Val | Asp | Ile | Phe | Ala | Glu | Asn | Asn | Ile | Gly | Ser |
| 705 |  |  |  |  | 710 |  |  |  |  | 715 |  |  |  |  | 720 |
| Ser | Asn | Pro | Ala | Phe | Ser | His | Glu | Leu | Val | Thr | Leu | Pro | Glu | Ser | Gln |
|  |  |  |  | 725 |  |  |  |  | 730 |  |  |  |  | 735 |  |

| | | | | | | | | | | | | |
|---|---|---|---|---|---|---|---|---|---|---|---|---|
|Ala|Pro|Ala|Asp<br>740|Leu|Gly|Gly|Gly|Lys<br>745|Met|Leu|Leu|Ile<br>750|Ala|Ile|Leu|

Ala Pro Ala Asp Leu Gly Gly Gly Lys Met Leu Leu Ile Ala Ile Leu
        740                 745                750

Gly Ser Ala Gly Met Thr Cys Leu Thr Val Leu Leu Ala Phe Leu Ile
        755             760                 765

Ile Leu Gln Leu Lys Arg Ala Asn Val Gln Arg Met Ala Gln Ala
770                 775             780

Phe Gln Asn Val Arg Glu Glu Pro Ala Val Gln Phe Asn Ser Gly Thr
785                 790             795                 800

Leu Ala Leu Asn Arg Lys Val Lys Asn Asn Pro Asp Pro Thr Ile Tyr
            805             810                 815

Pro Val Leu Asp Trp Asn Asp Ile Lys Phe Gln Asp Val Ile Gly Glu
            820             825             830

Gly Asn Phe Gly Gln Val Leu Lys Ala Arg Ile Lys Lys Asp Gly Leu
        835                 840             845

Arg Met Asp Ala Ala Ile Lys Arg Met Lys Glu Tyr Ala Ser Lys Asp
    850             855             860

Asp His Arg Asp Phe Ala Gly Glu Leu Glu Val Leu Cys Lys Leu Gly
865             870             875             880

His His Pro Asn Ile Ile Asn Leu Leu Gly Ala Cys Glu His Arg Gly
                885             890                 895

Tyr Leu Tyr Leu Ala Ile Glu Tyr Ala Pro His Gly Asn Leu Leu Asp
        900             905                 910

Phe Leu Arg Lys Ser Arg Val Leu Glu Thr Asp Pro Ala Phe Ala Ile
        915             920             925

Ala Asn Ser Thr Ala Ser Thr Leu Ser Ser Gln Gln Leu Leu His Phe
    930             935                 940

Ala Ala Asp Val Ala Arg Gly Met Asp Tyr Leu Ser Gln Lys Gln Phe
945             950             955             960

Ile His Arg Asp Leu Ala Ala Arg Asn Ile Leu Val Gly Glu Asn Tyr
            965                 970             975

Val Ala Lys Ile Ala Asp Phe Gly Leu Ser Arg Gly Gln Glu Val Tyr
        980             985             990

Val Lys Lys Thr Met Gly Arg Leu Pro Val Arg Trp Met Ala Ile Glu
    995             1000            1005

Ser Leu Asn Tyr Ser Val Tyr Thr Thr Asn Ser Asp Val Trp Ser Tyr
    1010            1015            1020

Gly Val Leu Leu Trp Glu Ile Val Ser Leu Gly Gly Thr Pro Tyr Cys
1025            1030            1035            1040

Gly Met Thr Cys Ala Glu Leu Tyr Glu Lys Leu Pro Gln Gly Tyr Arg
            1045            1050            1055

Leu Glu Lys Pro Leu Asn Cys Asp Asp Glu Val Tyr Asp Leu Met Arg
        1060            1065            1070

Gln Cys Trp Arg Glu Lys Pro Tyr Glu Arg Pro Ser Phe Ala Gln Ile
        1075            1080            1085

Leu Val Ser Leu Asn Arg Met Leu Glu Glu Arg Lys Thr Tyr Val Asn
    1090            1095            1100

Thr Thr Leu Tyr Glu Lys Phe Thr Tyr Ala Gly Ile Asp Cys Ser Ala
1105            1110            1115            1120

Glu Glu Ala Ala ( 2 ) INFORMATION FOR SEQ ID NO:3:

( i ) SEQUENCE CHARACTERISTICS:
( A ) LENGTH: 239 amino acids
( B ) TYPE: amino acid
( D ) TOPOLOGY: linear (i i) MOLECULE TYPE: protein (x i) SEQUENCE DESCRIPTION: SEQ ID NO:3:

| Val | Pro | Trp | Leu | Gly | Ala | Cys | Glu | His | Arg | Gly | Tyr | Leu | Tyr | Leu | Ala |
|---|---|---|---|---|---|---|---|---|---|---|---|---|---|---|---|
| 1 | | | | 5 | | | | | 10 | | | | | 15 | |

| Ile | Glu | Tyr | Ala | Pro | His | Gly | Asn | Leu | Leu | Asp | Phe | Leu | Arg | Lys | Ser |
|---|---|---|---|---|---|---|---|---|---|---|---|---|---|---|---|
| | | | 20 | | | | | 25 | | | | | 30 | | |

| Arg | Val | Leu | Glu | Thr | Asp | Pro | Ala | Phe | Ala | Ile | Ala | Asn | Ser | Thr | Ala |
|---|---|---|---|---|---|---|---|---|---|---|---|---|---|---|---|
| | | 35 | | | | | 40 | | | | | 45 | | | |

| Ser | Ile | Met | Ser | Ser | Gln | Gln | Leu | Leu | His | Phe | Ala | Ala | Asp | Val | Ala |
|---|---|---|---|---|---|---|---|---|---|---|---|---|---|---|---|
| | 50 | | | | 55 | | | | | 60 | | | | | |

| Arg | Gly | Met | Asp | Tyr | Leu | Ser | Gln | Lys | Gln | Phe | Ile | His | Arg | Asp | Leu |
|---|---|---|---|---|---|---|---|---|---|---|---|---|---|---|---|
| 65 | | | | | 70 | | | | | 75 | | | | | 80 |

| Ala | Ala | Arg | Asn | Ile | Leu | Val | Gly | Glu | Asn | Tyr | Ile | Ala | Lys | Ile | Ala |
|---|---|---|---|---|---|---|---|---|---|---|---|---|---|---|---|
| | | | | 85 | | | | | 90 | | | | | 95 | |

| Asp | Phe | Gly | Leu | Ser | Arg | Gly | Gln | Glu | Val | Tyr | Val | Lys | Lys | Thr | Met |
|---|---|---|---|---|---|---|---|---|---|---|---|---|---|---|---|
| | | | 100 | | | | | 105 | | | | | 110 | | |

| Gly | Arg | Leu | Pro | Val | Arg | Trp | Met | Ala | Ile | Glu | Ser | Leu | Asn | Tyr | Ser |
|---|---|---|---|---|---|---|---|---|---|---|---|---|---|---|---|
| | | 115 | | | | | 120 | | | | | 125 | | | |

| Val | Tyr | Thr | Thr | Asn | Ser | Asp | Val | Trp | Ser | Tyr | Gly | Val | Leu | Leu | Trp |
|---|---|---|---|---|---|---|---|---|---|---|---|---|---|---|---|
| | 130 | | | | | 135 | | | | | 140 | | | | |

| Glu | Ile | Val | Ser | Leu | Gly | Gly | Thr | Pro | Tyr | Cys | Gly | Met | Thr | Cys | Ala |
|---|---|---|---|---|---|---|---|---|---|---|---|---|---|---|---|
| 145 | | | | | 150 | | | | | 155 | | | | | 160 |

| Glu | Leu | Tyr | Glu | Lys | Leu | Pro | Gln | Gly | Tyr | Arg | Leu | Glu | Lys | Pro | Leu |
|---|---|---|---|---|---|---|---|---|---|---|---|---|---|---|---|
| | | | | 165 | | | | | 170 | | | | | 175 | |

| Asn | Cys | Asp | Asp | Glu | Val | Tyr | Asp | Leu | Met | Arg | Gln | Cys | Trp | Arg | Glu |
|---|---|---|---|---|---|---|---|---|---|---|---|---|---|---|---|
| | | | 180 | | | | | 185 | | | | | 190 | | |

| Lys | Pro | Tyr | Glu | Arg | Pro | Ser | Phe | Ala | Gln | Ile | Leu | Val | Ser | Leu | Asn |
|---|---|---|---|---|---|---|---|---|---|---|---|---|---|---|---|
| | | 195 | | | | | 200 | | | | | 205 | | | |

| Arg | Met | Leu | Glu | Glu | Arg | Lys | Thr | Tyr | Val | Asn | Thr | Thr | Leu | Tyr | Glu |
|---|---|---|---|---|---|---|---|---|---|---|---|---|---|---|---|
| | 210 | | | | | 215 | | | | | 220 | | | | |

| Lys | Phe | Thr | Tyr | Ala | Gly | Ile | Asp | Cys | Ser | Ala | Glu | Glu | Ala | Ala |
|---|---|---|---|---|---|---|---|---|---|---|---|---|---|---|
| 225 | | | | | 230 | | | | | 235 | | | | |

(2) INFORMATION FOR SEQ ID NO:4:

(i) SEQUENCE CHARACTERISTICS:
(A) LENGTH: 8 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:4:

| Asp | Tyr | Lys | Asp | Asp | Asp | Asp | Lys |
|---|---|---|---|---|---|---|---|
| 1 | | | | 5 | | | |

(2) INFORMATION FOR SEQ ID NO:5:

(i) SEQUENCE CHARACTERISTICS:
(A) LENGTH: 11 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:5:

| Gly | Gly | Gly | Gly | Ser | Gly | Gly | Gly | Gly | Ser |
|---|---|---|---|---|---|---|---|---|---|
| 1 | | | | 5 | | | | | 10 |

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GATCTTGGAA CGAGACGACC TGCT                        24

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

AGCAGGTCGT CTCGTTCCAA                            20

( 2 ) INFORMATION FOR SEQ ID NO:8:

( i ) SEQUENCE CHARACTERISTICS:
        ( A ) LENGTH: 1138 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Met Val Trp Arg Val Pro Pro Phe Leu Leu Pro Ile Leu Phe Leu Ala
 1               5                  10                  15

Ser His Val Gly Ala Ala Val Asp Leu Thr Leu Leu Ala Asn Leu Arg
            20                  25                  30

Leu Thr Asp Pro Gln Arg Phe Phe Leu Thr Cys Val Ser Gly Glu Ala
        35                  40                  45

Gly Ala Gly Arg Gly Ser Asp Ala Trp Gly Pro Pro Leu Leu Leu Glu
    50                  55                  60

Lys Asp Asp Arg Ile Val Arg Thr Pro Pro Gly Pro Pro Leu Arg Leu
65                  70                  75                  80

Ala Arg Asn Gly Ser His Gln Val Thr Leu Arg Gly Phe Ser Lys Pro
                85                  90                  95

Ser Asp Leu Val Gly Val Phe Ser Cys Val Gly Gly Ala Gly Ala Arg
            100                 105                 110

Arg Thr Arg Val Ile Tyr Val His Asn Ser Pro Gly Ala His Leu Leu
        115                 120                 125

Pro Asp Lys Val Thr His Thr Val Asn Lys Gly Asp Thr Ala Val Leu
    130                 135                 140

Ser Ala Arg Val His Lys Glu Lys Gln Thr Asp Val Ile Trp Lys Ser
145                 150                 155                 160

Asn Gly Ser Tyr Phe Tyr Thr Leu Asp Trp His Glu Ala Gln Asp Gly
                165                 170                 175

Arg Phe Leu Leu Gln Leu Pro Asn Val Gln Pro Pro Ser Ser Gly Ile
            180                 185                 190

Tyr Ser Ala Thr Tyr Leu Glu Ala Ser Pro Leu Gly Ser Ala Phe Phe
        195                 200                 205
```

-continued

| | | | | | | | | | | | | | | |
|---|---|---|---|---|---|---|---|---|---|---|---|---|---|---|
| Arg | Leu 210 | Ile | Val | Arg | Gly 215 | Cys | Gly | Ala | Gly | Arg 220 | Trp | Gly | Pro | Gly | Cys |
| Thr 225 | Lys | Glu | Cys | Pro | Gly 230 | Cys | Leu | His | Gly | Gly 235 | Val | Cys | His | Asp | His 240 |
| Asp | Gly | Glu | Cys | Val 245 | Cys | Pro | Pro | Gly | Phe 250 | Thr | Gly | Thr | Arg | Cys 255 | Glu |
| Gln | Ala | Cys | Arg 260 | Glu | Gly | Arg | Phe | Gly 265 | Gln | Ser | Cys | Gln | Glu 270 | Gln | Cys |
| Pro | Gly | Ile 275 | Ser | Gly | Cys | Arg | Gly 280 | Leu | Thr | Phe | Cys | Leu 285 | Pro | Asp | Pro |
| Tyr | Gly 290 | Cys | Ser | Cys | Gly | Ser 295 | Gly | Trp | Arg | Gly | Ser 300 | Gln | Cys | Gln | Glu |
| Ala 305 | Cys | Ala | Pro | Gly | His 310 | Phe | Gly | Ala | Asp | Cys 315 | Arg | Leu | Gln | Cys 320 | Gln |
| Cys | Gln | Asn | Gly | Gly 325 | Thr | Cys | Asp | Arg | Phe 330 | Ser | Gly | Cys | Val | Cys 335 | Pro |
| Ser | Gly | Trp | His 340 | Gly | Val | His | Cys | Glu 345 | Lys | Ser | Asp | Arg | Ile 350 | Pro | Gln |
| Ile | Leu | Asn 355 | Met | Ala | Ser | Glu | Leu 360 | Glu | Phe | Asn | Leu | Glu 365 | Thr | Met | Pro |
| Arg | Ile 370 | Asn | Cys | Ala | Ala | Ala 375 | Gly | Asn | Pro | Phe | Pro 380 | Val | Arg | Gly | Ser |
| Ile 385 | Glu | Leu | Arg | Lys | Pro 390 | Asp | Gly | Thr | Val | Leu 395 | Leu | Ser | Thr | Lys | Ala 400 |
| Ile | Val | Glu | Pro | Glu 405 | Lys | Thr | Thr | Ala | Glu 410 | Phe | Glu | Val | Pro | Arg 415 | Leu |
| Val | Leu | Ala | Asp 420 | Ser | Gly | Phe | Trp | Glu 425 | Cys | Arg | Val | Ser | Thr 430 | Ser | Gly |
| Gly | Gln | Asp 435 | Ser | Arg | Arg | Phe | Lys 440 | Val | Asn | Val | Lys 445 | Val | Pro | Pro | Val |
| Pro 450 | Leu | Ala | Ala | Pro | Arg 455 | Leu | Leu | Thr | Lys | Gln 460 | Ser | Arg | Gln | Leu | Val |
| Val 465 | Ser | Pro | Leu | Val | Ser 470 | Phe | Ser | Gly | Asp | Gly 475 | Pro | Ile | Ser | Thr | Val 480 |
| Arg | Leu | His | Tyr | Arg 485 | Pro | Gln | Asp | Ser | Thr 490 | Met | Asp | Trp | Ser | Thr 495 | Ile |
| Val | Val | Asp | Pro 500 | Ser | Glu | Asn | Val | Thr 505 | Leu | Met | Asn | Leu | Arg 510 | Pro | Lys |
| Thr | Gly | Tyr 515 | Ser | Val | Arg | Val | Gln 520 | Leu | Ser | Arg | Pro | Gly 525 | Glu | Gly | Gly |
| Glu | Gly 530 | Ala | Trp | Gly | Pro | Pro 535 | Thr | Leu | Met | Thr | Thr 540 | Asp | Cys | Pro | Glu |
| Pro 545 | Leu | Leu | Gln | Pro | Trp 550 | Leu | Glu | Gly | Trp | His 555 | Val | Glu | Gly | Thr | Asp 560 |
| Arg | Leu | Arg | Val | Ser 565 | Trp | Ser | Leu | Pro | Leu 570 | Val | Pro | Gly | Pro | Leu 575 | Val |
| Gly | Asp | Gly | Phe 580 | Leu | Leu | Arg | Leu | Trp 585 | Asp | Gly | Thr | Arg | Gly 590 | Gln | Glu |
| Arg | Arg | Glu 595 | Asn | Val | Ser | Ser | Pro 600 | Gln | Ala | Arg | Thr | Ala 605 | Leu | Leu | Thr |
| Gly | Leu | Thr 610 | Pro | Gly | Thr | His | Tyr 615 | Gln | Leu | Asp | Val | Gln 620 | Leu | Tyr | His |
| Cys 625 | Thr | Leu | Leu | Gly | Pro 630 | Ala | Ser | Pro | Pro | Ala 635 | His | Val | Leu | Leu | Pro 640 |
| Pro | Ser | Gly | Pro | Pro | Ala | Pro | Arg | His | Leu | His | Ala | Gln | Ala | Leu | Ser |

|     |     |     | 645 |     |     |     |     | 650 |     |     |     |     | 655 |     |
|-----|-----|-----|-----|-----|-----|-----|-----|-----|-----|-----|-----|-----|-----|-----|
| Asp | Ser | Glu | Ile | Gln | Leu | Thr | Trp | Lys | His | Pro | Glu | Ala | Leu | Pro | Gly |
|     |     |     | 660 |     |     |     | 665 |     |     |     | 670 |     |     |     |

Pro Ile Ser Lys Tyr Val Val Glu Val Gln Val Ala Gly Gly Ala Gly
675 680 685

Asp Pro Leu Trp Ile Asp Val Asp Arg Pro Glu Glu Thr Ser Thr Ile
690 695 700

Ile Arg Gly Leu Asn Ala Ser Thr Arg Tyr Leu Phe Arg Met Arg Ala
705 710 715 720

Ser Ile Gln Gly Leu Gly Asp Trp Ser Asn Thr Val Glu Glu Ser Thr
725 730 735

Leu Gly Asn Gly Leu Gln Ala Glu Gly Pro Val Gln Glu Ser Arg Ala
740 745 750

Ala Glu Glu Gly Leu Asp Gln Gln Leu Ile Leu Ala Val Val Gly Ser
755 760 765

Val Ser Ala Thr Cys Leu Thr Ile Leu Ala Ala Leu Leu Thr Leu Val
770 775 780

Cys Ile Arg Arg Ser Cys Leu His Arg Arg Arg Thr Phe Thr Tyr Gln
785 790 795 800

Ser Gly Ser Gly Glu Glu Thr Ile Leu Gln Phe Ser Ser Gly Thr Leu
805 810 815

Thr Leu Thr Arg Arg Pro Lys Leu Gln Pro Glu Pro Leu Ser Tyr Pro
820 825 830

Val Leu Glu Trp Glu Asp Ile Thr Phe Glu Asp Leu Ile Gly Glu Gly
835 840 845

Asn Phe Gly Gln Val Ile Arg Ala Met Ile Lys Lys Asp Gly Leu Lys
850 855 860

Met Asn Ala Ala Ile Lys Met Leu Lys Glu Tyr Ala Ser Glu Asn Asp
865 870 875 880

His Arg Asp Phe Ala Gly Glu Leu Glu Val Leu Cys Lys Leu Gly His
885 890 895

His Pro Asn Ile Ile Asn Leu Leu Gly Ala Cys Lys Asn Arg Gly Tyr
900 905 910

Leu Tyr Ile Ala Ile Glu Tyr Ala Pro Tyr Gly Asn Leu Leu Asp Phe
915 920 925

Leu Arg Lys Ser Arg Val Leu Glu Thr Asp Pro Ala Phe Ala Arg Glu
930 935 940

His Gly Thr Ala Ser Thr Leu Ser Ser Arg Gln Leu Leu Arg Phe Ala
945 950 955 960

Ser Asp Ala Ala Asn Gly Met Gln Tyr Leu Ser Glu Lys Gln Phe Ile
965 970 975

His Arg Asp Leu Ala Ala Arg Asn Val Leu Val Gly Glu Asn Leu Ala
980 985 990

Ser Lys Ile Ala Asp Phe Gly Leu Ser Arg Gly Glu Glu Val Tyr Val
995 1000 1005

Lys Lys Thr Met Gly Arg Leu Pro Val Arg Trp Met Ala Ile Glu Ser
1010 1015 1020

Leu Asn Tyr Ser Val Tyr Thr Thr Lys Ser Asp Val Trp Ser Phe Gly
1025 1030 1035 1040

Val Leu Leu Trp Glu Ile Val Ser Leu Gly Gly Thr Pro Tyr Cys Gly
1045 1050 1055

Met Thr Cys Ala Glu Leu Tyr Glu Lys Leu Pro Gln Ala Asp Arg Met
1060 1065 1070

Glu Gln Pro Arg Asn Cys Asp Asp Glu Val Tyr Glu Leu Met Arg Gln
1075 1080 1085

```
Cys Trp Arg Asp Arg Pro Tyr Glu Arg Pro Pro Phe Ala Gln Ile Ala
    1090            1095            1100

Leu Gln Leu Gly Arg Met Leu Glu Ala Arg Lys Ala Tyr Val Asn Met
1105            1110            1115                    1120

Ser Leu Phe Glu Asn Phe Thr Tyr Ala Gly Ile Asp Ala Thr Ala Glu
            1125            1130            1135

Glu Ala
```